United States Patent [19]

Diehr et al.

[11] Patent Number: 4,780,126
[45] Date of Patent: Oct. 25, 1988

[54] 3-SUBSTITUTED 1-(2-HALOGENOALKOXY-BENZENESULPHONYL)-3-HETEROARYL-(THIO)UREAS

[75] Inventors: Hans-Joachim Diehr; Christa Fest, both of Wuppertal; Rolf Kirsten, Monheim; Joachim Kluth, Langenfeld; Klaus-Helmut Müller, Düsseldorf; Theodor Pfister, Monheim; Uwe Priesnitz, Solingen; Hans-Jochem Riebel, Wuppertal; Wolfgang Roy, Langenfeld; Hans-Joachim Santel, Köln; Robert R. Schmidt, Bergisch-Gladbach; Ludwig Eue, Leverkusen; Ernst Kysela, Bergisch-Gladbach, all of Fed. Rep. of Germany

[73] Assignee: Bayer Aktiengesellschaft, Leverkusen, Fed. Rep. of Germany

[21] Appl. No.: 60,187

[22] Filed: Jun. 9, 1987

Related U.S. Application Data

[63] Continuation-in-part of Ser. No. 769,186, Aug. 23, 1985, abandoned.

[30] Foreign Application Priority Data

Aug. 30, 1984 [DE]  Fed. Rep. of Germany ....... 3431917
Jun. 26, 1986 [DE]  Fed. Rep. of Germany ....... 3621320

[51] Int. Cl.$^4$ ................ C07D 251/42; C07D 251/46; A01N 43/66
[52] U.S. Cl. ......................................... 71/93; 544/211
[58] Field of Search ............................ 544/211; 71/93

[56] References Cited

U.S. PATENT DOCUMENTS

H1,68    12/1986  Conner ..................... 71/93
4,452,628  6/1984  Adams ..................... 71/93
4,537,619  8/1985  Meyer et al. .............. 71/93

FOREIGN PATENT DOCUMENTS 81-4874  1/1982  South Africa .

Primary Examiner—John M. Ford
Attorney, Agent, or Firm—Sprung Horn Kramer & Woods

[57] ABSTRACT

3-Substituted 1-(2-halogenoalkoxy-benzenesulphonyl)-3-heteroaryl-(thio)urea herbicides of the formula

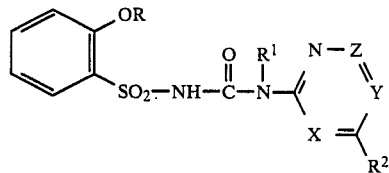

in which
(A)
  R is $CF_3$,
  Q is O,
  $R^1$ is $CH_3$, $C_2H_5$, $C_3H_7$-n, $C_3H_7$-i, $CH_2-CH=CH_2$, $CH_2-C\equiv CH$ or $CH_2-C_6H_5$,
  $R^2$ is $CH_3$, $OCH_3$, $OC_2H_5$, $SCH_3$, $NH-CH_3$ or $NH-C_2H_5$,
  X is N,
  Y is N and
  Z is $C-CH_3$, $C-C_2H_5$, $C-OCH_3$ or $C-OC_2H_5$; or
(B)
  R is $CF_3$,
  Q is O,
  $R^1$ is $CH_3$, $C_2H_5$, $C_3H_7$-n, $C_3H_7$-i, $CH_2-CH=CH_2$, $CH_2-C\equiv CH$ or $CH_2-C_6H_5$,
  $R^2$ is $CH_3$, $OCH_3$ or $OC_2H_5$,
  X is N,
  Y is C—H and
  Z is $C-C_2H_5$, $C-OCH_3$ or $C-OC_2H_5$; or
(C)
  R is $CH_2-CH_2Cl$,
  Q is O,
  $R^1$ is $CH_3$, $C_2H_5$, $C_3H_7$-n, $C_3H_7$-i, $CH_2-CH=CH_2$, $CH_2-C\equiv CH$ or $CH_2-C_6H_5$,
  $R^2$ is $CH_3$, $OCH_3$, $OC_2H_5$, $SCH_3$, $NH-CH_3$ or $NH-C_2H_5$,
  X is N,
  Y is N and
  Z is $C-CH_3$, $C-C_2H_5$, $C-OCH_3$ or $C-OC_2H_5$; or
(D)
  R is $CH_2-CH_2Cl$,
  Q is O,
  $R^1$ is $CH_3$, $C_2H_5$, $C_3H_7$-n, $C_3H_7$-i, $CH_2-CH=CH_2$, $CH_2-C\equiv CH$ or $CH_2-C_6H_5$,
  $R^2$ is $CH_3$, $OCH_3$ or $OC_2H_5$,
  X is N,
  Y is C—H and
  Z is $C-CH_3$, $C-C_2H_5$, $C-OCH_3$ or $C-OC_2H_5$; or
(E)
  R is $CHF_2$,
  Q is O,
  $R^1$ is $CH_3$,
  $R^2$ is $CH_3$,
  X is N,
  Y is N and
  Z is $C-CH_3$, or a salt thereof with a metal or basic organic nitrogen compound.

7 Claims, No Drawings

3-SUBSTITUTED 1-(2-HALOGENOALKOXY-BENZENESUL-PHONYL)-3-HETEROARYL-(THIO)UREAS

This application is a continuation-in-part of application Ser. No. 769,186, filed Aug. 23, 1985, now abandoned.

The invention relates to new 3-substituted 1-(2-halogenoalkoxy-benzenesulphonyl)-3-heteroaryl-(thio)ureas, several processes for their preparation and their use as herbicides.

It is known that certain 1-arylsulphonyl-3-heteroaryl-ureas, such as, for example, 1-(2-methoxy-benzenesulphonyl)-3-(4,6-dimethyl-pyrimidin-2-yl)urea, 1-(2-trifluoromethoxy-benzenesulphonyl)-3-(4,6-dimethoxy-pyrimidin-2-yl)urea and 1-(2-trifluoromethoxybenzenesulphonyl)-3-(4,6-dimethyl-pyrimidin-2-yl)urea, have a herbicidal action. However, the action of these compounds is not always completely satisfactory (compare, for example, U.S. Pat. No. 4,169,719 and European Pat. No. A-173,312).

New 3-substituted 1-(2-halogenoalkoxy-benzenesulphonyl)-3-heteroaryl-(thio)ureas of the general formula (I)

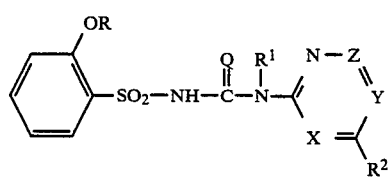

in which
R represents halogenoalkyl,
Q represents oxygen or sulphur,
$R^1$ represents optionally substituted radicals from the series comprising alkyl, alkenyl, alkinyl or aralkyl,
$R^2$ represents hydrogen, halogen, hydroxyl, alkyl, halogenoalkyl, alkoxy, halogenoalkoxy, alkylthio, halogenoalkylthio, amino, alkylamino or dialkylamino,
X represents nitrogen or a —CH— grouping,
Y represents nitrogen or a —$CR^3$— grouping, wherein
$R^3$ represents hydrogen, halogen, cyano, alkyl, formyl, alkyl-carbonyl or alkoxy-carbonyl and
Z represents nitrogen or a —$CR^4$— grouping, wherein
$R^4$ represents hydrogen, halogen, hydroxyl, alkyl, halogenoalkyl, alkoxy, halogenoalkoxy, alkylthio, alkylamino or dialkylamino,
and salts of compounds of the formula (I) with metals and basic organic nitrogen compounds have now been found.

The new 3-substituted 1-(2-halogenoalkoxy-benzenesulphonyl)-3-heteroaryl-(thio)ureas of the formula (I) are obtained by a process in which (a) 2-halogenoalkoxy-benzenesulphonyl iso(thio)cyanates of the formula (II)

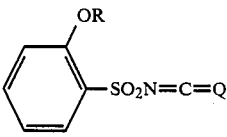

in which
Q and R have the abovementioned meanings, are reacted with heteroarylamines of the formula (III)

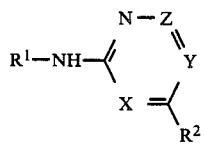

in which
$R^1$, $R^2$, X, Y and Z have the abovementioned meanings, if appropriate in the presence of diluents and if appropriate in the presence of catalysts, and, if appropriate, the products thus obtained are converted into salts by customary methods, or by a process in which (b) 2-halogenoalkoxy-benzenesulphonic acid amides of the formula (IV)

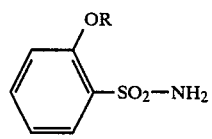

in which
R has the abovementioned meanings, are reacted with N-heteroaryl-urethanes of the formula (V)

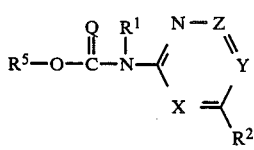

in which
$R^1$, $R^2$, Q, X, Y and Z have the abovementioned meanings, and
$R^5$ represents $C_1$-$C_4$-alkyl, benzyl or phenyl,
if appropriate in the presence of diluents and if appropriate in the presence of acid acceptors, and, if appropriate, the products thus obtained are converted into salts by customary methods, or by a process in which (c) N-(2-halogenoalkoxy-benzenesulphonyl)-urethanes of the formula (VI)

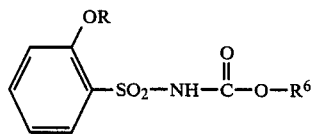

in which
Q and R have the abovementioned meanings and
$R^6$ represents $C_1$-$C_4$-alkyl, benzyl or phenyl, are reacted with heteroarylamines of the formula (III)

$$R^1-NH-\overset{N=Z}{\underset{X=\underset{R^2}{}}{}}Y \quad (III)$$

in which

R¹, R², X, Y and Z have the abovementioned meanings, if appropriate in the presence of diluents and if appropriate in the presence of acid acceptors, and, if appropriate, the products thus obtained are converted into salts by customary methods, or by a process in which (d) 1-arylsulphonyl-3-heteroaryl-ureas of the formula (VII)

$$\underset{}{\text{[benzene ring with OR]}}-SO_2-NH-\overset{O}{\underset{}{C}}-NH-\overset{N=Z}{\underset{X=\underset{R^2}{}}{}}Y \quad (VII)$$

in which

Q, R, R², X, Y and Z have the abovementioned meanings, are reacted with compounds of the formula (VIII)

$$R^1-W \quad (VIII)$$

in which

R¹ has the abovementioned meanings and

W represents a nucleophilic leaving group, if appropriate in the presence of diluents and if appropriate in the presence of acid acceptors, and, if appropriate, the products thus obtained are converted into salts by customary methods.

THe new 3-substituted 1-(2-halogenoalkoxy-benzenesulphonyl)-3-heteroaryl-(thio)ureas of the formula (I) are distinguished by a potent herbicidal activity.

Surprisingly, the new compounds of the formula (I) exhibit a considerably better herbicidal action than the already known urea derivatives of the same type of action.

The invention preferably relates to compounds of the formula (I) in which

R represents halogeno-$C_1$-$C_4$-alkyl,

Q represents oxygen or sulphur,

R¹ represents $C_1$-$C_6$-alkyl [which is optionally substituted by fluorine, cyano, $C_1$-$C_4$-alkoxy or $C_1$-$C_4$-alkylthio], or represents $C_3$-$C_6$-alkenyl or $C_3$-$C_6$-alkinyl [which are optionally substituted by fluorine or chlorine], or represents phenyl-$C_1$-$C_2$-alkyl [which is optionally substituted in the phenyl part by fluorine, chlorine, nitro, cyano, methyl, methoxy or $C_1$-$C_2$-alkoxycarbonyl], R² represents hydrogen, fluorine, chlorine, bromine, methyl, trifluoromethyl, methoxy, ethoxy, difluoromethoxy methylthio, ethylthio, amino, methylamino, ethylamino, dimethylamino or diethylamino.

X represents nitrogen or a —CH— grouping,

Y represents nitrogen or a —CR³— grouping, wherein

R³ represents hydrogen, fluorine, chlorine, bromine, methyl, formyl, acetyl, methoxycarbonyl or ethoxycarbonyl, and Z represents nitrogen or a —CR⁴— grouping, wherein R⁴ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

The invention furthermore preferably relates to salts of compounds of the formula (I)—as defined above with sodium, potassium, magnesium or calcium and with monoalkyl-, dialkyl-, trialkyl-, benzyl-alkyl- and benzyl-dialkylamines with in each case up to 4 carbon atoms in the alkyl radicals, the alkyl radicals optionally in each case containing a substituent from the series comprising fluorine, chlorine, hydroxyl, methoxy, ethoxy and cyano.

Compounds of the formula (I) which are particularly preferred are those in which R represents trifluoromethyl, difluoromethyl, 2-chloroethyl or 1,1,2,2-tetrafluoroethyl, Q represents oxygen or sulphur, R¹ represents methyl, ethyl, n-propyl, i-propyl, n-butyl, allyl, propargyl, benzyl or phenylethyl and R², X, Y and Z have the abovementioned preferred meanings.

If, for example, 2-trifluoromethoxy-benzenesulphonyl isothiocyanate and 4-ethoxy-6-methyl-2-methylamino-1,3,5-triazine are used as starting substances for process variant (a), the course of the reaction can be outlined by the following equation:

[Reaction scheme showing 2-trifluoromethoxy-benzenesulphonyl isothiocyanate + methylamino-triazine derivative → thiourea product]

If, for example, 2-difluoromethoxy-benzenesulphonic acid amide and O-phenyl-N-methyl-N-(4-ethylamino-6-methylthio-1,3,5-triazin-2-yl)-urethane are used as starting substances for process variant (b), the course of the reaction can be outlined by the following equation:

[Reaction scheme with OCHF₂-benzenesulphonamide + urethane starting material]

-continued

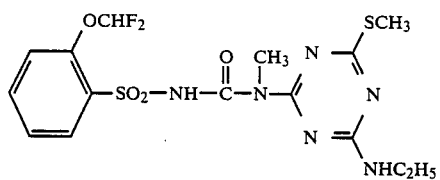

If, for example, O-phenyl-N-[2-(2-chloroethoxy)benzenesulphonyl]-urethane and 2-benzylamino-4-chloro-6-methoxy-pyrimidine are used as starting substances for process variant (c), the course of the reaction can be outlined by the following equation:

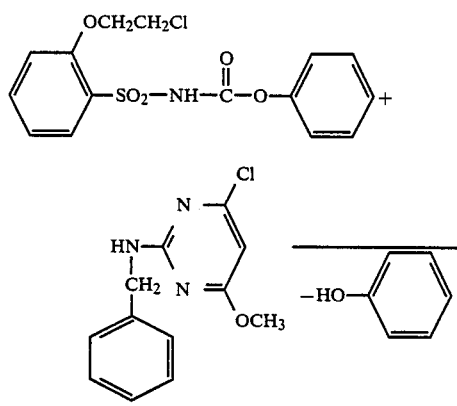

If, for example, 1-(2-trifluoromethoxy-benzenesulphonyl)-3-(4,6-dimethoxy-1,3,5-triazin-2-yl)-urea and methyl iodide are used as starting substances for process variant (d), the course of the reaction can be outlined by the following equation:

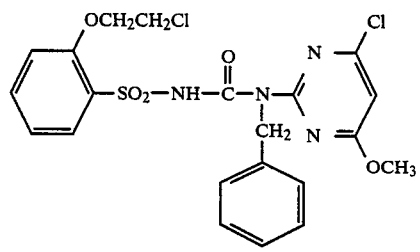

Formula (II) provides a general definition of the 2-halogenoalkoxy-benzenesulphonyl iso(thio)cyanates to be used as starting substances in process (a) according to the invention. In this formula (II), Q and R preferably or particularly represent those radicals which have already been mentioned as preferred or as particularly preferred for these substituents in connection with the description of the substancs of the formula (I) according to the invention.

Examples of the compounds of the formula (II) which may be mentioned are: 2-trifluoromethoxy-, 2-(2-chloroethoxy)-, 2-difluoromethoxy- and 2-(1,1,2,2-tetrafluoroethoxy-benzenesulphonyl isocyanate and -benzenesulphonyl isothiocyanate.

The compounds of the formula (II) are known and/or can be prepared by known processes (compare, for example, European Pat. Nos. A-44,808 and 173,312 and U.S. Pat. No. 4,514,212).

Formula (III) provides a general definition of the heteroarylamines also to be used as starting substances in process (a) according to the invention. In this formula (III), $R^1$, $R^2$, X, Y and Z preferably or particularly represent those radicals which have already been mentioned as preferred or as particularly preferred for these substituents in connection with the description of the substances of the formula (I) according to the invention.

Examples which may be mentioned of the compounds of the formula (III) are:

TABLE 1

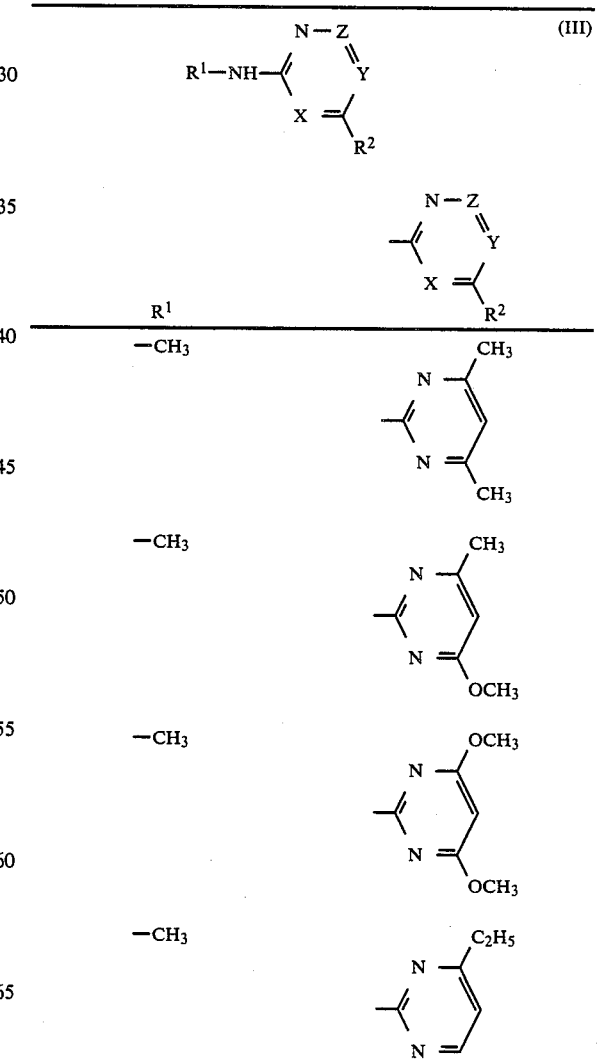

TABLE 1-continued $$\underset{R^1-NH}{\overset{N-Z}{\underset{X}{\bigvee}}\underset{R^2}{\overset{Y}{\bigvee}}} \quad (III)$$

| R¹ | (ring structure) |
|---|---|
| —CH₃ | pyrimidine with 4-OC₂H₅, 6-OC₂H₅ |
| —CH₃ | 1,3,5-triazine with OCH₃, CH₃ |
| —CH₃ | pyrimidine with 2-OCH₃, 4-OCH₃ |
| —CH₃ | pyrimidine with 2-CH₃, 4-CH₃ |
| —CH₃ | pyrimidine with 4-CH₃ |
| —CH₃ | pyrazine with CH₃, CH₃ |
| —CH₃ | pyrimidine with 4-CH₃, 6-Cl |
| —CH₃ | 1,3,5-triazine with OCH₃, OCH₃ |
| —CH₃ | 1,3,5-triazine with OC₂H₅, CH₃ |
| —CH₃ | 1,3,5-triazine with OC₂H₅, OCH₃ |
| —CH₃ | pyrimidine with OCHF₂, CH₃ |
| —CH₃ | 1,3,5-triazine with CH₃, SC₂H₅ |
| —CH₃ | 1,3,5-triazine with OCH₃, SCH₃ |
| —CH₃ | 1,3,5-triazine with OC₂H₅, SCH₃ |

TABLE 1-continued $$R^1-NH-\underset{X}{\overset{N-Z}{\underset{\underset{R^2}{|}}{\diagdown}}}Y \quad (III)$$

| R¹ | ![structure](N-Z/X-Y/R²) |
|---|---|
| —CH₃ | 4-OCH₃, 6-SC₂H₅ triazine |
| —CH₃ | 4-OC₂H₅, 6-OC₂H₅ triazine |
| —CH₃ | 4-CH₃, 6-SCH₃ triazine |
| —CH₃ | 4-CH₃, 6-N(CH₃)₂ triazine |
| —CH₃ | 4-CH₃, 6-N(C₂H₅)₂ triazine |
| —CH₃ | 4-OCH₃, 6-NHCH₃ triazine |
| —CH₃ | 4-OCH₃, 6-NHC₂H₅ triazine |
| —CH₃ | 4-OCH₃, 6-N(CH₃)₂ triazine |
| —CH₃ | 4-CF₃, 6-Cl pyrimidine |
| —CH₃ | 4-OC₂H₅, 6-SC₂H₅ triazine |
| —CH₃ | 4-CH₃, 6-NHCH₃ triazine |
| —CH₃ | 4-CH₃, 6-NHC₂H₅ triazine |
| —CH₃ | 4-OC₂H₅, 6-N(C₂H₅)₂ triazine |
| —CH₃ | 4-SCH₃, 6-NHCH₃ triazine |

(Note: structural diagrams in the original table depict substituted 1,3,5-triazine and pyrimidine rings with the substituents shown at the 4- and 6-positions; the 2-position bears a methyl group attached to the R¹-NH-C= of formula III.)

TABLE 1-continued $$\underset{R^1-NH}{\overset{N-Z}{\underset{X}{\bigvee}}}\underset{R^2}{\overset{Y}{\bigvee}} \quad (III)$$

| R¹ | ![structure](N-Z/X-Y/R²) |
|---|---|
| —CH₃ | 2-methyl-4-(SCH₃)-6-(NHC₂H₅)-1,3,5-triazine |
| —CH₃ | 2-methyl-4-(OCH₃)-6-Cl-pyrimidine |
| —CH₃ | 2-methyl-4-(OCH₃)-6-N(C₂H₅)₂-1,3,5-triazine |
| —CH₃ | 2-methyl-4-(OC₂H₅)-6-NHCH₃-1,3,5-triazine |
| —CH₃ | 2-methyl-4-(OC₂H₅)-6-NHC₂H₅-1,3,5-triazine |
| —CH₃ | 2-methyl-4-(OC₂H₅)-6-N(CH₃)₂-1,3,5-triazine |
| —CH₃ | 3-methyl-6-methyl-1,2,4-triazine |
| —CH₃ | 2,6-dimethyl-4-methyl-pyridine |
| —CH₃ | 2-methyl-4-(SCH₃)-6-N(CH₃)₂-1,3,5-triazine |
| —CH₃ | 2-methyl-4-(SC₂H₅)-6-NHCH₃-1,3,5-triazine |
| —CH₃ | 2-methyl-4-(SC₂H₅)-6-N(C₂H₅)₂-1,3,5-triazine |
| —CH₂—C₆H₅ | 2-methyl-4,6-dimethyl-pyrimidine |
| —CH₂—C₆H₅ | 2-methyl-4-methyl-6-OCH₃-pyrimidine |
| —CH₂—C₆H₅ | 2-methyl-4,6-di(OCH₃)-pyrimidine |

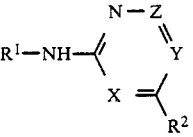

TABLE 1-continued $$\underset{X}{\overset{N-Z}{\underset{\parallel}{R^1-NH-C}}}\overset{Y}{\underset{R^2}{\parallel}}\quad\text{(III)}$$

| $R^1$ | $\overset{N-Z}{\underset{X}{\parallel}}\overset{Y}{\underset{R^2}{\parallel}}$ |
|---|---|
| —CH₂—C₆H₅ | 2-methyl-4,6-bis(OC₂H₅)-pyrimidine |
| —CH₃ | 2-methyl-4-SCH₃-6-N(C₂H₅)₂-1,3,5-triazine |
| —CH₃ | 2-methyl-4-SC₂H₅-6-N(CH₃)₂-1,3,5-triazine |
| —CH₃ | 3-methyl-5,6-dimethyl-1,2,4-triazine |
| —CH₂—C₆H₅ | 2-methyl-4-CH₃-pyrimidine |
| —CH₂—C₆H₅ | 2-methyl-4-C₂H₅-pyrimidine |
| —CH₂—C₆H₅ | 2-methyl-4-OCHF₂-6-CH₃-pyrimidine |
| —CH₃ | 2-methyl-4-OC₂H₅-6-Cl-pyrimidine |
| —CH₂—C₆H₅ | 2,4,6-trimethyl-1,3,5-triazine |
| —CH₂—C₆H₅ | 2-methyl-4-OCH₃-6-CH₃-1,3,5-triazine |
| —CH₂—C₆H₅ | 2-methyl-4,6-bis(OC₂H₅)-1,3,5-triazine |
| —CH₂—C₆H₅ | 2-methyl-4-CH₃-6-SCH₃-1,3,5-triazine |
| —C₂H₅ | 2-methyl-4,6-dimethyl-pyrimidine |
| —C₂H₅ | 2-methyl-4-CH₃-6-OCH₃-pyrimidine |
| —C₂H₅ | 2-methyl-4,6-bis(OCH₃)-pyrimidine |

*Note: The right column structures are drawn as pyrimidine/triazine ring diagrams in the original; textual descriptions provided here for clarity.*

TABLE 1-continued $$R^1-NH-\overset{N-Z}{\underset{X}{\overset{\|}{C}}}\overset{Y}{\underset{R^2}{}} \quad (III)$$

| R¹ | ![structure] |
|---|---|
| –CH₂–C₆H₅ | pyrimidine with OCH₃, OCH₃ (triazine N positions) |
| –CH₂–C₆H₅ | pyrimidine with OC₂H₅, CH₃ |
| –CH₂–C₆H₅ | triazine with OC₂H₅, OCH₃ |
| –C₂H₅ | pyrimidine with OCH₃, OCH₃ |
| –C₂H₅ | pyrimidine with CH₃, CH₃ |
| –C₂H₅ | pyrimidine with CH₃ |
| –C₂H₅ | pyrimidine with OC₂H₅, OC₂H₅ |
| –CH₃ | pyrimidine with OCHF₂, CF₃ |
| –C₂H₅ | pyrimidine with C₂H₅ |
| –C₂H₅ | triazine with OCH₃, CH₃ |
| –C₂H₅ | triazine with OC₂H₅, CH₃ |
| –C₂H₅ | triazine with OC₂H₅, OCH₃ |
| –C₂H₅ | pyrimidine with OCHF₂, CH₃ |
| –CH₃ | pyrimidine with C₂H₅, Cl |

TABLE 1-continued
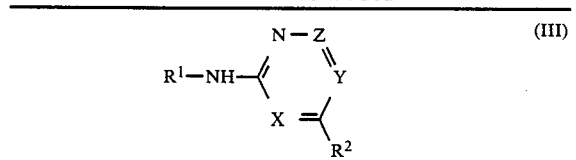
(III)
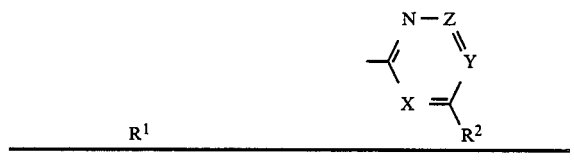
| R¹ | |
|---|---|
| —CH₃ | 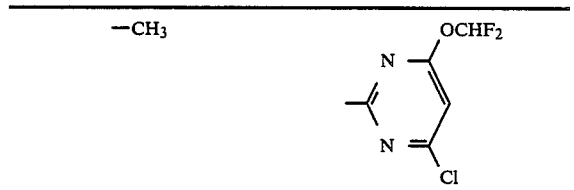 |
| —C₂H₅ | 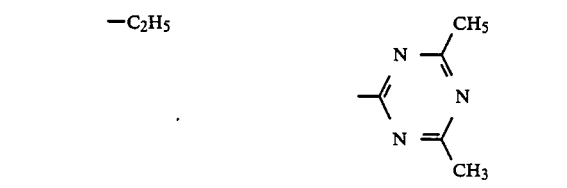 |
| —C₂H₅ | 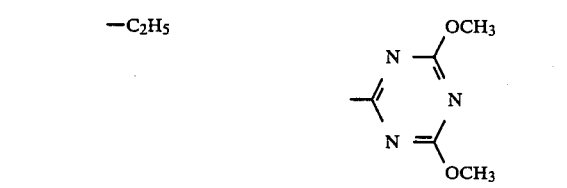 |
| —C₂H₅ | 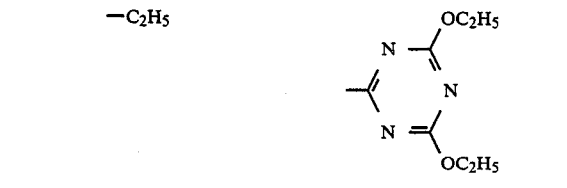 |
| —C₂H₅ | 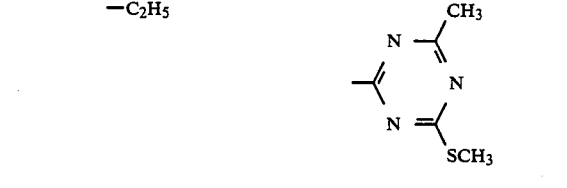 |
| —C₂H₅ | 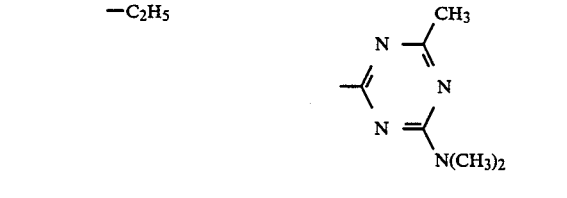 |
| —C₂H₅ |  |
TABLE 1-continued
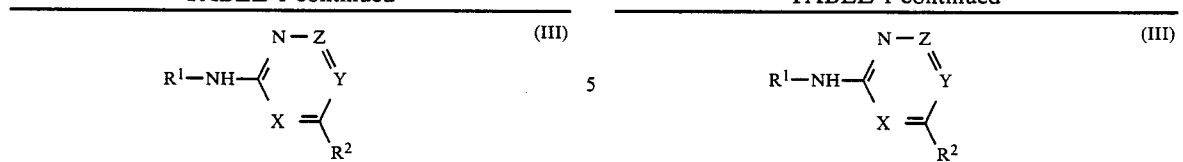
(III)
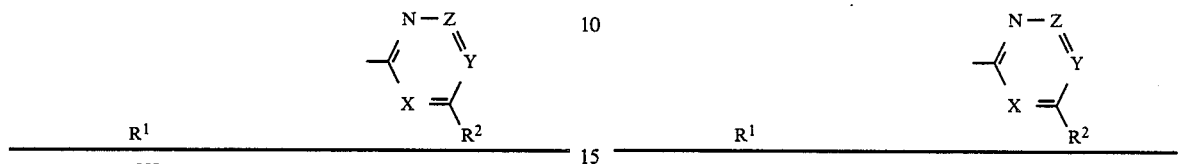
| R¹ | |
|---|---|
| —C₂H₅ | 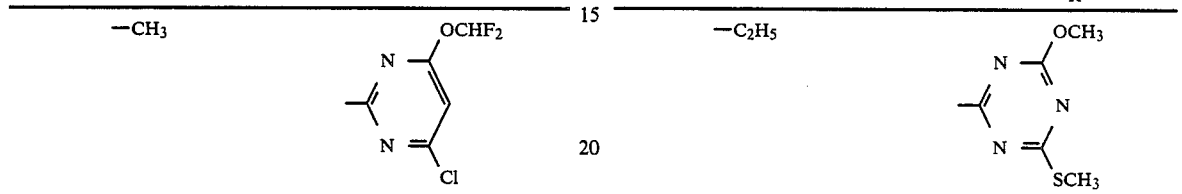 |
| —C₂H₅ | 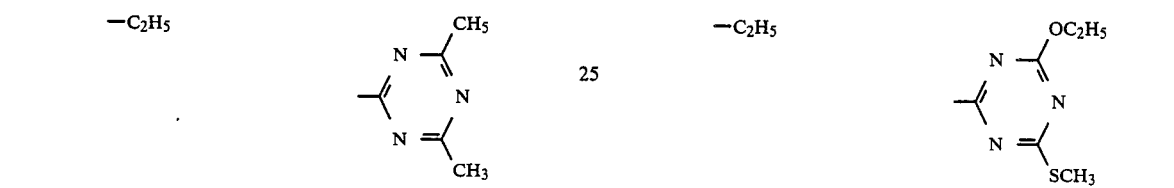 |
| —C₂H₅ | 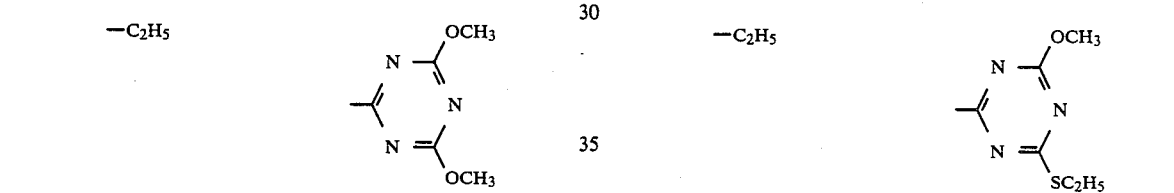 |
| —C₂H₅ | 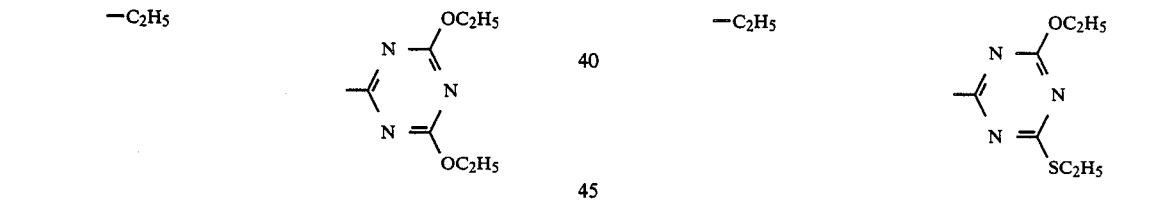 |
| —C₂H₅ | 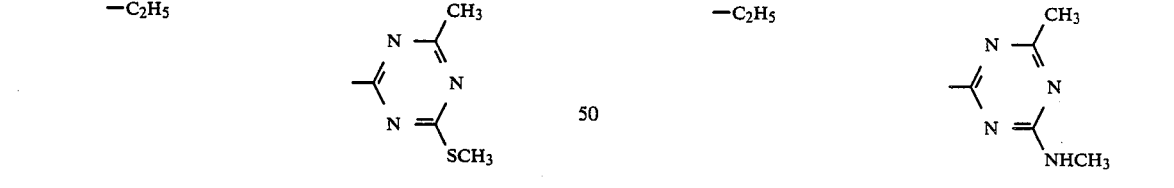 |
| —C₂H₅ | 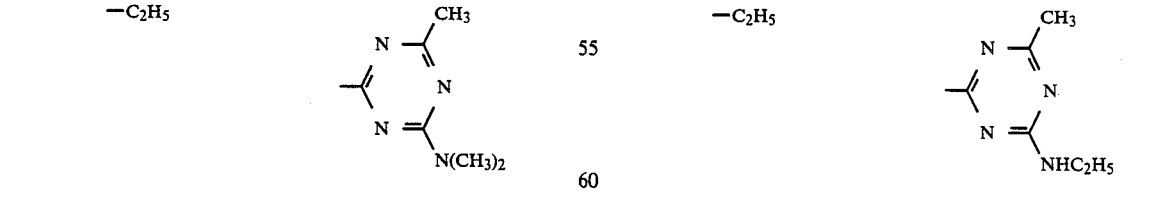 |
| —C₂H₅ | 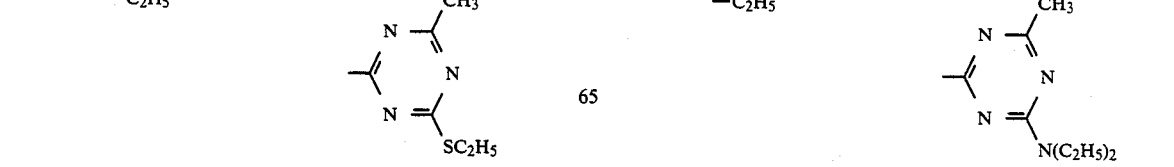 |

TABLE 1-continued $$R^1-NH-\underset{X}{\overset{N-Z}{\underset{\|}{C}}}\underset{R^2}{\overset{Y}{\|}}$$ (III)

| $R^1$ | ![ring](N-Z, X, Y, R²) |
|---|---|
| —C₂H₅ | triazine with OCH₃ and NHCH₃ |
| —C₂H₅ | triazine with OCH₃ and NHC₂H₅ |
| —C₂H₅ | triazine with OCH₃ and N(CH₃)₂ |
| —C₂H₅ | triazine with OCH₃ and N(C₂H₅)₂ |
| —C₂H₅ | triazine with OC₂H₅ and NHCH₃ |
| —C₂H₅ | triazine with OC₂H₅ and NHC₂H₅ |
| —C₂H₅ | triazine with OC₂H₅ and N(C₂H₅)₂ |
| —C₂H₅ | triazine with SCH₃ and NHCH₃ |
| —C₂H₅ | triazine with SCH₃ and NHC₂H₅ |
| —C₂H₅ | triazine with SCH₃ and N(CH₃)₂ |
| —C₂H₅ | triazine with SC₂H₅ and NHCH₃ |
| —C₂H₅ | triazine with SC₂H₅ and N(C₂H₅)₂ |
| —C₂H₅ | triazine with SCH₃ and SCH₃ |
| —C₂H₅ | triazine with OC₂H₅ and N(CH₃)₂ |

TABLE 1-continued $$R^1-NH-\underset{X}{\overset{N-Z}{\underset{R^2}{\vert\vert}}}Y \quad (III)$$

| $R^1$ | ![structure](N-Z/X-Y/R²) |
|---|---|
| —C₂H₅ | 3-methyl-6-methyl-1,2,4-triazine |
| —C₂H₅ | 2,4-dimethyl pyridine |
| —C₂H₅ | 2-methyl-4-SCH₃-6-N(C₂H₅)₂-1,3,5-triazine |
| —C₂H₅ | 2-methyl-4-SC₂H₅-6-N(CH₃)₂-1,3,5-triazine |
| —C₂H₅ | 3-methyl-5-CH₃-6-CH₃-1,2,4-triazine |
| —C₂H₅ | 2-methyl-4-SC₂H₅-6-SC₂H₅-pyrimidine |
| —CH₃ | 2-methyl-4-CF₃-6-OCH₃-pyrimidine |
| —CH₃ | 2-methyl-4-CF₃-6-CH₃-pyrimidine |
| —CH₃ | 2-methyl-4-C₂H₅-6-OCH₃-pyrimidine |
| —C₃H₇—n | 2-methyl-4-CH₃-6-CH₃-pyrimidine |
| —C₃H₇—n | 2-methyl-4-CH₃-6-OCH₃-pyrimidine |
| —C₃H₇—n | 2-methyl-4-OCH₃-6-OCH₃-pyrimidine |
| —C₃H₇—n | 2-methyl-4-OC₂H₅-6-OC₂H₅-pyrimidine |
| —CH₂—C₆H₅ | 2-methyl-4-OCH₃-6-Cl-pyrimidine |

TABLE 1-continued

Structure (III):

$$R^1-NH-C(=N-Z)(X)-C(Y)=C(R^2)-$$  (also shown with X/Y swapped)

| R¹ | Ring system |
|---|---|
| —CH₂—C₆H₅ | pyrimidine with Cl (4-), CH₃ (6-) |
| —CH₂—C₆H₅ | pyrimidine with Cl (4-), OCH₃ (6-) |
| —C₃H₇—n | pyrimidine with CH₃ (4-) |
| —C₃H₇—n | pyrimidine with C₂H₅ (4-) |
| —C₃H₇—n | pyrimidine with OCHF₂ (4-), CH₃ (6-) |
| —C₃H₇—n | triazine with OCH₃, OCH₃ |
| —C₃H₇—n | pyrimidine with CH₃, CH₃ |
| —C₃H₇—n | triazine with OCH₃, CH₃ |
| —C₃H₇—n | triazine with OC₂H₅, OC₂H₅ |
| —CH₂—CH=CH₂ | pyrimidine with CH₃, CH₃ |
| —CH₂—CH=CH₂ | pyrimidine with CH₃, OCH₃ |
| —CH₂—CH=CH₂ | pyrimidine with OCH₃, OCH₃ |
| —CH₂—CH=CH₂ | triazine with CH₃, CH₃ |
| —C₃H₇—n | triazine with CH₃, SCH₃ |

TABLE 1-continued $$R^1-NH-C(X=)-... \quad (III)$$
(structure with N—Z, Y, X, R²)

| R¹ | (heterocycle) |
|---|---|
| —C₃H₇—n | triazine with OC₂H₅, N, CH₃ |
| —C₃H₇—n | triazine with OC₂H₅, N, OCH₃ |
| —CH₂—CH=CH₂ | pyrimidine with CH₃ |
| —CH₂—CH=CH₂ | pyrimidine with C₂H₅ |
| —CH₂—CH=CH₂ | pyrimidine with OCHF₂, CH₃ |
| —CH₂—CH=CH₂ | pyrimidine with OCH₃, OCH₃ |
| —CH₂—CH=CH₂ | pyrimidine with OCH₃, CH₃ |
| —CH₂—CH=CH₂ | triazine with OC₂H₅, N, OC₂H₅ |
| —CH₂—CH=CH₂ | triazine with CH₃, N, SCH₃ |
| —CH₂—CH=CH₂ | triazine with OC₂H₅, N, CH₃ |
| —CH₂—CH=CH₂ | triazine with OC₂H₅, N, OCH₃ |

The compounds of the formula (III) are known and can be prepared by processes which are known per se (compare, for example, Chem. Pharm. Bull. 11 (1963), 1382 and U.S. Pat. No. 4,299,960, European Pat. Nos. A-121,082, 125,205 and 126,711 and European Pat. No. A-152,378).

Formula (IV) provides a general definition of the 2-halogenoalkoxy-benzenesulphonic acid amides to be used as starting substances in process (b) according to the invention. In this formula (IV), R preferably or particularly represents those radicals which have already been mentioned as preferred or as particularly preferred for this substituent in connection with the description of the substances of the formula (I) according to the invention.

Examples which may be mentioned of the compounds of the formula (IV) are: 2-trifluoromethoxy-, 2-difluoromethoxy-, 2-(2-chloroethoxy)- and 2-(1,1,2,2-tetrafluoroethoxy)-benzenesulphonic acid amide.

The compounds of the formula (IV) are known (compare, for example, Zh. Org. Khim. [J. Org. Chem. USSR], 8 (1972), 1023–1026 [English 1032–1034] and European Pat. No. A-44,808).

Formula (V) provides a general definition of the N-heteroaryl-urethanes also to be used as starting substances in process (b) according to the invention. In this formula (V), $R^1$, $R^2$, X, Y, Z and Q preferably or particularly represent those radicals which have already been mentioned as preferred or as particularly preferred for these substituents in connection with the description of the substances of the formula (I) according to the invention. $R^5$ in this formula preferably represents methyl, benzyl or phenyl, in particular methyl or phenyl.

Examples which may be mentioned of the compounds of the formula (V) are:

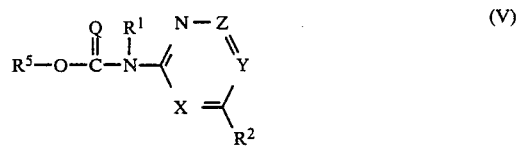

(V)

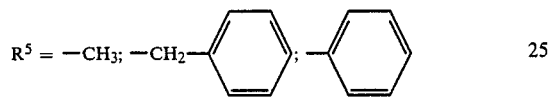

Q = O or S

TABLE 2

| $R^1$ | |
|---|---|
| —CH₃ | 4,6-dimethyl-pyrimidin-2-yl |
| —CH₃ | 4,6-dimethoxy-pyrimidin-2-yl |
| —CH₃ | 4-methyl-6-methoxy-pyrimidin-2-yl |
| —CH₃ | 4-methoxy-6-methoxy-pyrimidin-2-yl |

TABLE 2-continued

| $R^1$ | ring |
|---|---|
| —CH₃ | 4-ethyl-pyrimidin-2-yl (C₂H₅) |
| —CH₃ | 4,6-diethoxy-pyrimidin-2-yl (OC₂H₅, OC₂H₅) |
| —CH₃ | 4-methoxy-6-methyl-1,3,5-triazin-2-yl (OCH₃, CH₃) |
| —CH₃ | 4-ethoxy-6-methyl-1,3,5-triazin-2-yl (OC₂H₅, CH₃) |
| —CH₃ | 4-ethoxy-6-methoxy-1,3,5-triazin-2-yl (OC₂H₅, OCH₃) |
| —CH₃ | 4,6-dimethyl-1,3,5-triazin-2-yl (CH₃, CH₃) |
| —CH₃ | 4-methyl-6-methoxy-1,3,5-triazin-2-yl (CH₃, OCH₃) |
| —CH₃ | 4,6-dimethyl-1,3,5-triazin-2-yl (CH₃, CH₃) |

TABLE 2-continued

| R¹ | ![structure](N-Z/X-Y/R²) |
|---|---|
| —CH₃ | 4-methyl-6-chloropyrimidin-2-yl (CH₃ at 4, Cl at 6) |
| —CH₃ | 4,6-dimethoxy-1,3,5-triazin-2-yl |
| —CH₃ | 4,6-diethoxy-1,3,5-triazin-2-yl |
| —CH₃ | 4-methyl-6-methylthio-1,3,5-triazin-2-yl |
| —CH₃ | 4-difluoromethoxy-6-methylpyrimidin-2-yl |
| —CH₃ | 4-methyl-6-ethylthio-1,3,5-triazin-2-yl |
| —CH₃ | 4-methoxy-6-methylthio-1,3,5-triazin-2-yl |
| —CH₃ | 4-ethoxy-6-methylthio-1,3,5-triazin-2-yl |

TABLE 2-continued

| R¹ | ![structure](N-Z/X-Y/R²) |
|---|---|
| —CH₃ | 4-methoxy-6-ethylthio-1,3,5-triazin-2-yl |
| —CH₃ | 4-trifluoromethyl-6-chloropyrimidin-2-yl |
| —CH₃ | 4-ethoxy-6-ethylthio-1,3,5-triazin-2-yl |
| —CH₃ | 4-methyl-6-dimethylamino-1,3,5-triazin-2-yl |
| —CH₃ | 4-methyl-6-diethylamino-1,3,5-triazin-2-yl |
| —CH₃ | 4-methoxy-6-methylamino-1,3,5-triazin-2-yl |
| —CH₃ | 4-methoxy-6-ethylamino-1,3,5-triazin-2-yl |
| —CH₃ | 4-methoxy-6-dimethylamino-1,3,5-triazin-2-yl |

TABLE 2-continued

![structure: N—Z, Y, X, R²]

| R¹ | structure |
|---|---|
| —CH₃ | pyrimidine with OCH₃ and Cl substituents |
| —CH₃ | triazine with OCH₃ and N(C₂H₅)₂ |
| —CH₃ | triazine with CH₃ and NHCH₃ |
| —CH₃ | triazine with CH₃ and NHC₂H₅ |
| —CH₃ | triazine with OC₂H₅ and N(C₂H₅)₂ |
| —CH₃ | triazine with SCH₃ and NHCH₃ |
| —CH₃ | triazine with SCH₃ and NHC₂H₅ |
| —CH₃ | triazine with SCH₃ and N(CH₃)₂ |

TABLE 2-continued

| R¹ | structure |
|---|---|
| —CH₃ | triazine with SC₂H₅ and NHCH₃ |
| —CH₃ | triazine with OC₂H₅ and NHCH₃ |
| —CH₃ | triazine with OC₂H₅ and NHC₂H₅ |
| —CH₃ | triazine with OC₂H₅ and N(CH₃)₂ |
| —CH₃ | triazine with CH₃ (1,2,4-triazine) |
| —CH₃ | pyridine with two CH₃ substituents |
| —CH₃ | triazine with SCH₃ and N(C₂H₅)₂ |
| —CH₃ | triazine with SC₂H₅ and N(CH₃)₂ |

TABLE 2-continued
| R¹ | (heterocycle with N-Z, X, Y, R²) |
|---|---|
| —CH₃ | 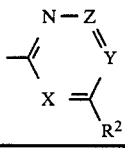 |
| —CH₂—C₆H₅ | 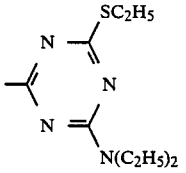 |
| —CH₂—C₆H₅ | 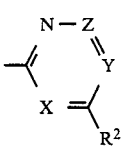 |
| —CH₂—C₆H₅ | 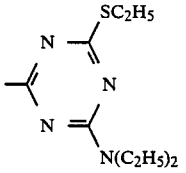 |
| —CH₂—C₆H₅ | 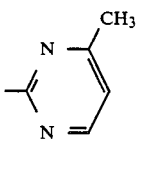 |
| —CH₂—C₆H₅ | 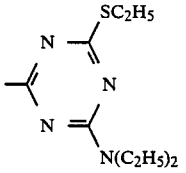 |
| —CH₂—C₆H₅ | 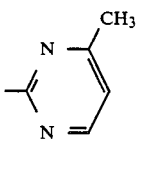 |
| —CH₃ | 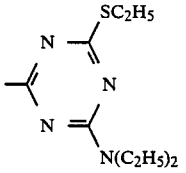 |
| —CH₂—C₆H₅ | 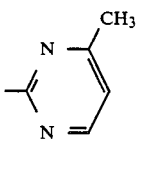 |
| —CH₂—C₆H₅ | 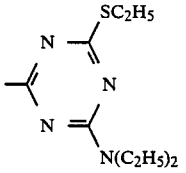 |
| —CH₂—C₆H₅ | 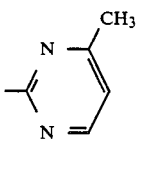 |
| —CH₃ | 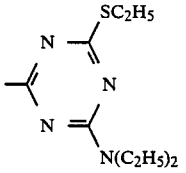 |
| —CH₂—C₆H₅ | 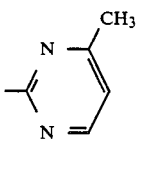 |
| —CH₂—C₆H₅ | 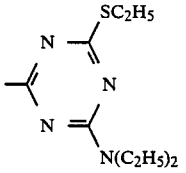 |
| —CH₂—C₆H₅ | 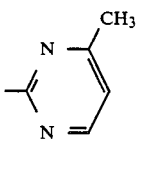 |

TABLE 2-continued
| R¹ | |
|---|---|
| —C₂H₅ | 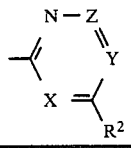 |
| —C₂H₅ | 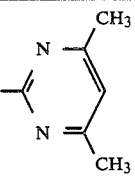 |
| —C₂H₅ | 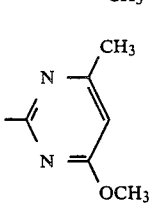 |
| —C₂H₅ | 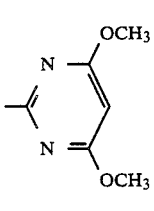 |
| —CH₃ | 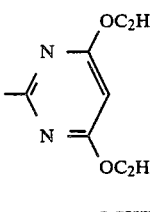 |
| —CH₂—C₆H₅ | 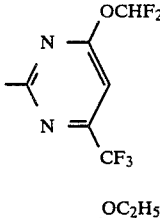 |
| —C₂H₅ | 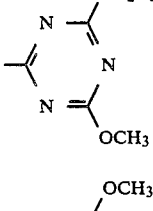 |
| —C₂H₅ | 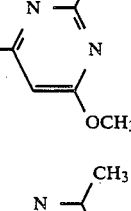 |
TABLE 2-continued
| R¹ | |
|---|---|
| —C₂H₅ | 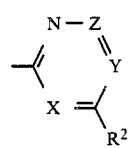 |
| —CH₃ | 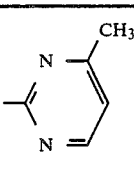 |
| —CH₃ | 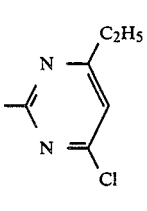 |
| —C₂H₅ | 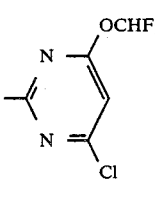 |
| —C₂H₅ | 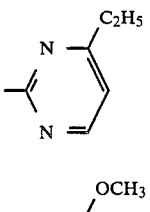 |
| —C₂H₅ | 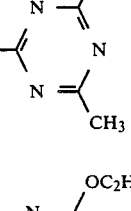 |
| —C₂H₅ | 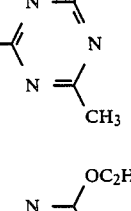 |
| —C₂H₅ | 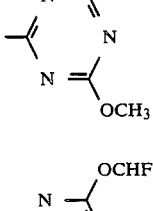 |

TABLE 2-continued

| R¹ | (heterocycle with substituents) |
|---|---|
| —C₂H₅ | triazine: CH₃, SC₂H₅ |
| —C₂H₅ | triazine: OCH₃, SCH₃ |
| —C₂H₅ | triazine: CH₃, CH₃ |
| —C₂H₅ | triazine: OCH₃, OCH₃ |
| —C₂H₅ | triazine: OC₂H₅, OC₂H₅ |
| —C₂H₅ | triazine: CH₃, SCH₃ |
| —C₂H₅ | triazine: CH₃, N(CH₃)₂ |
| —C₂H₅ | triazine: CH₃, N(C₂H₅)₂ |
| —C₂H₅ | triazine: OCH₃, NHCH₃ |
| —C₂H₅ | triazine: OC₂H₅, SCH₃ |
| —C₂H₅ | triazine: OCH₃, SC₂H₅ |
| —C₂H₅ | triazine: OC₂H₅, SC₂H₅ |
| —C₂H₅ | triazine: CH₃, NHCH₃ |
| —C₂H₅ | triazine: CH₃, NHC₂H₅ |
| —C₂H₅ | triazine: OC₂H₅, N(C₂H₅)₂ |
| —C₂H₅ | triazine: SCH₃, NHCH₃ |

TABLE 2-continued

R¹ — heterocycle (N=Z, X, Y, R²)

| R¹ | Heterocycle substituents |
|---|---|
| —C₂H₅ | triazine: OCH₃, NHC₂H₅ |
| —C₂H₅ | triazine: OCH₃, N(CH₃)₂ |
| —C₂H₅ | triazine: OCH₃, N(C₂H₅)₂ |
| —C₂H₅ | triazine: OC₂H₅, NHCH₃ |
| —C₂H₅ | triazine: OC₂H₅, NHC₂H₅ |
| —C₂H₅ | triazine: OC₂H₅, N(CH₃)₂ |
| —C₂H₅ | pyridazine: CH₃ |
| —C₂H₅ | triazine: SCH₃, NHC₂H₅ |
| —C₂H₅ | triazine: SCH₃, N(CH₃)₂ |
| —C₂H₅ | triazine: SC₂H₅, NHCH₃ |
| —C₂H₅ | triazine: SC₂H₅, N(C₂H₅)₂ |
| —C₂H₅ | triazine: SCH₃, SCH₃ |
| —C₂H₅ | triazine: CF₃, OCH₃ |
| —C₂H₅ | pyrazine: CF₃, CH₃ |
| —C₂H₅ | pyridine: CH₃, CH₃ |
| —C₂H₅ | triazine: SCH₃, N(C₂H₅)₂ |

TABLE 2-continued

![heterocycle with N—Z, X, Y, R²]

| R¹ | R² |
|---|---|
| —C₂H₅ | 2-methyl-4-(SC₂H₅)-6-[N(CH₃)₂]-1,3,5-triazine |
| —C₂H₅ | 3-methyl-5,6-dimethyl-1,2,4-triazine |
| —C₂H₅ | 2-methyl-4,6-bis(SC₂H₅)-1,3,5-triazine |
| —CH₂—C₆H₅ | 2-methyl-4-OCH₃-6-Cl-pyrimidine |
| —CH₂—C₆H₅ | 2-methyl-4-Cl-6-CH₃-pyrimidine |
| —CH₃ | 2-methyl-4-C₂H₅-6-OCH₃-pyrimidine |
| —C₃H₇—n | 2-methyl-4,6-dimethyl-pyrimidine |
| —C₃H₇—n | 2-methyl-4-CH₃-6-OCH₃-pyrimidine |
| —C₃H₇—n | 2-methyl-4,6-dimethoxy-pyrimidine |
| —C₃H₇—n | 2-methyl-4,6-bis(OC₂H₅)-pyrimidine |
| —C₃H₇—n | 2-methyl-4,6-dimethyl-1,3,5-triazine |
| —C₃H₇—n | 2-methyl-4-OCH₃-6-methyl-1,3,5-triazine |
| —CH₂—C₆H₅ | 2-methyl-4-Cl-6-OCH₃-pyrimidine |
| —C₃H₇—n | 2-methyl-4-CH₃-pyrimidine |
| —C₃H₇—n | 2-methyl-4-C₂H₅-pyrimidine |
| —C₃H₇—n | 2-methyl-4-OCHF₂-6-CH₃-pyrimidine |

TABLE 2-continued

![header structure with N—Z, Y, X, R²]

| R¹ | (heterocycle) |
|---|---|
| —C₃H₇—n | N=C(OCH₃)−N=C(OCH₃) triazine |
| —C₃H₇—n | N=C(CH₃)−N=C(SCH₃) triazine |
| —C₃H₇—n | N=C(OC₂H₅)−N=C(CH₃) triazine |
| —C₃H₇—n | N=C(OC₂H₅)−N=C(OC₂H₅) triazine |
| —CH₂—CH=CH₂ | pyrimidine 4,6-di-CH₃ |
| —CH₂—CH=CH₂ | pyrimidine 4-CH₃, 6-OCH₃ |
| —CH₂—CH=CH₂ | pyrimidine 4,6-di-OCH₃ |
| —CH₂—CH=CH₂ | N=C(CH₃)−N=C(CH₃) triazine |
| —CH₂—CH=CH₂ | N=C(OCH₃)−N=C(CH₃) triazine |
| —CH₂—CH=CH₂ | N=C(OC₂H₅)−N=C(OC₂H₅) triazine |
| —C₃H₇—n | N=C(OC₂H₅)−N=C(OCH₃) triazine |
| —CH₂—CH=CH₂ | pyrimidine 4-CH₃ |
| —CH₂—CH=CH₂ | pyrimidine 4-C₂H₅ |
| —CH₂—CH=CH₂ | pyrimidine 4-OCHF₂, 6-CH₃ |
| —CH₂—CH=CH₂ | N=C(OCH₃)−N=C(OCH₃) triazine |
| —CH₂—CH=CH₂ | N=C(OC₂H₅)−N=C(CH₃) triazine |

TABLE 2-continued

| R¹ | ![structure with N-Z, X, Y, R²] |
|---|---|
| —CH₂—CH=CH₂ | pyrimidine with OC₂H₅ and OCH₃ |
| —CH₂—CH=CH₂ | triazine with CH₃ and SCH₃ |

The compounds of the formula (V) are known and can be prepared by processes which are known per se (compare, for example, European Pat. Nos. A-101,670, 121,082, 125,205, 126,711 and European Pat. No. A-152,378).

Formula (VI) provides a general definition of the N-(2-halogenoalkoxy-benzenesulphonyl)-urethanes to be used as starting substances in process (c) according to the invention. In this formula (VI), R and Q preferably or particularly represent those radicals which have already been mentioned as preferred or as particularly preferred for these substituents in connecton with the description of the substances of the formula (I) according to the invention. $R^6$ in formula (VI) preferably represents methyl, benzyl or phenyl, in particular methyl or phenyl.

Examples which may be mentioned of the compounds of the formula (VI) are: N-(2-trifluoromethoxy-benzenesulphonyl)-, N-[2-(2-chloroethoxy)-benzenesulphonyl]-, N-(2-difluoromethoxy-benzenesulphonyl)-, N-[2-(1,1,2,2-tetrafluoroethoxy)-benzenesulphonyl]-O-methyl-urethane, -O-phenyl-urethane, -O-methyl-thiourethane and -O-phenyl-thiourethane.

The compounds of the formula (VI) are known (compare, for example, European Pat. Nos. A-125,205, 121,082, 44,808 and European Pat. No. A-44,809).

The heteroarylamines of the formula (III) also to be used as starting substances in process (c) according to the invention have already been described in the description of process variant (a).

Formula (VII) provides a general definition of the 1-arylsulphonyl-3-heteroaryl-ureas to be used as starting substances in process (d) according to the invention. In this formula (VII), R, $R^2$, Q, X, Y and Z preferably or particularly represent those radicals which have already been mentioned as preferred or as particularly preferred for these substituents in connection with the description of the substances of the formula (I) according to the invention.

Examples which may be mentioned of the compounds of the formula (VII) are:

TABLE 3

(VII)

Phenyl-OR with ortho SO₂—NH—C(=O)—NH—C(=N-Z / X=Y / R²) structure

| R | Q | R² |
|---|---|---|
| —CF₃ | O | pyrimidine with CH₃ (top) and CH₃ (bottom) |
| —CF₃ | O | pyrimidine with CH₃ and OCH₃ |
| —CF₃ | O | pyrimidine with OCH₃ and OCH₃ |
| —CF₃ | O | pyrimidine with C₂H₅ and (lower substituent) |
| —CF₃ | O | pyrimidine with OC₂H₅ and OC₂H₅ |
| —CF₃ | O | triazine with OCH₃ and CH₃ |
| —CF₃ | O | triazine with OC₂H₅ and CH₃ |

TABLE 3-continued
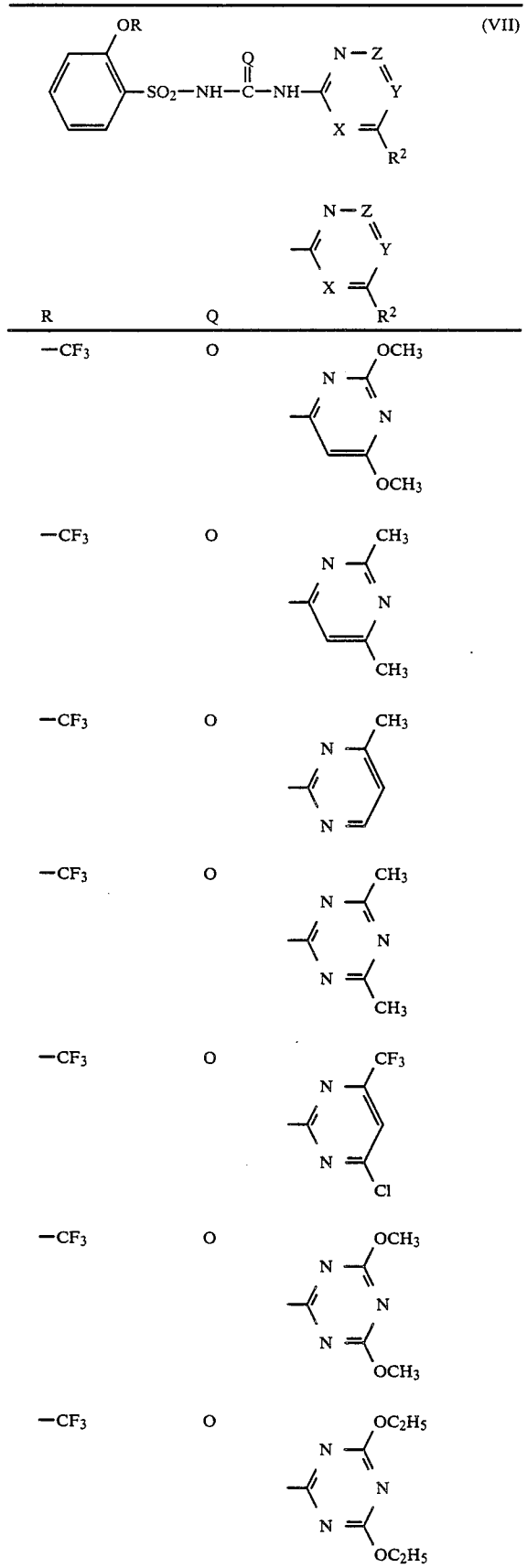
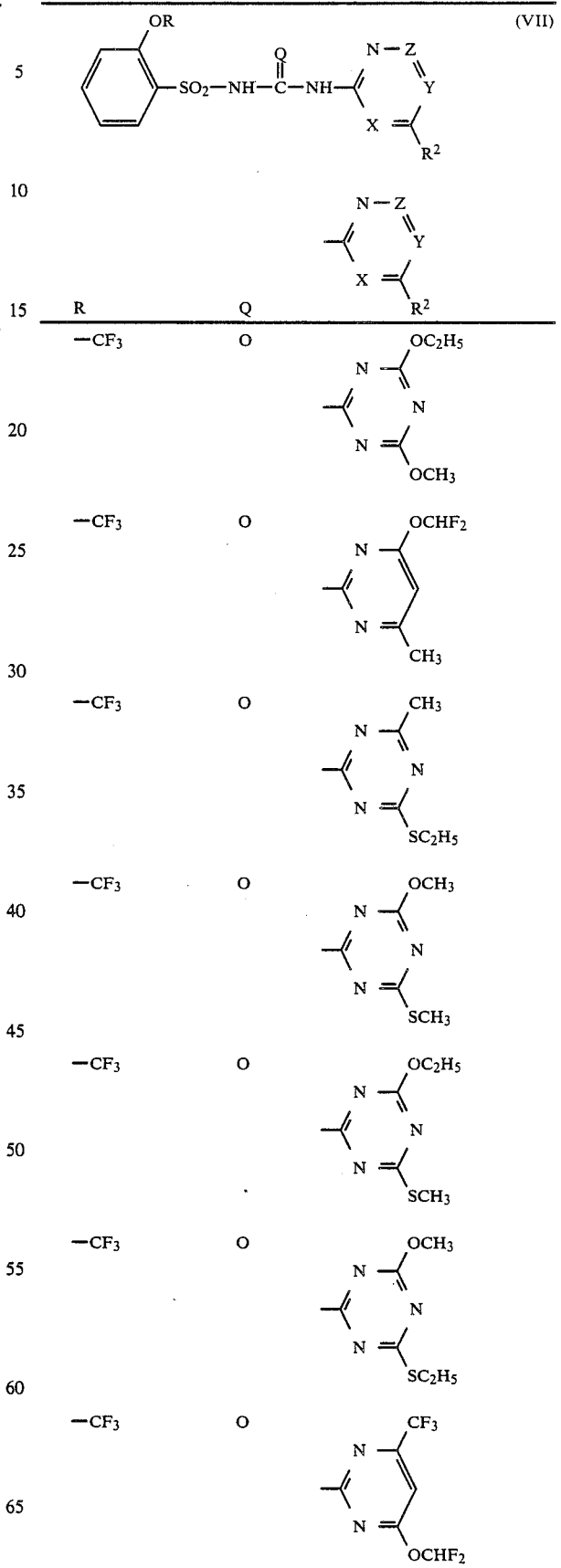

TABLE 3-continued
(VII)
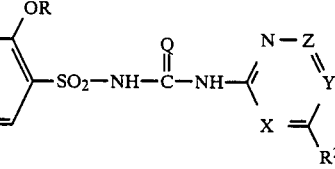
| R | Q | (substituent) |
|---|---|---|
| —CF₃ | O | 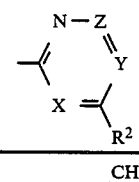 |
| —CF₃ | O | 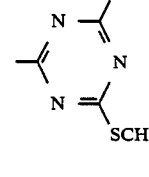 |
| —CF₃ | O | 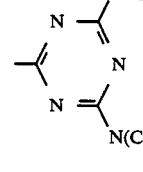 |
| —CF₃ | O | 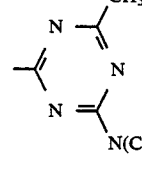 |
| —CF₃ | O | 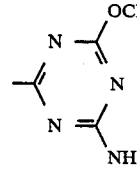 |
| —CF₃ | O | 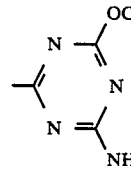 |
| —CF₃ | O | 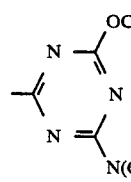 |
TABLE 3-continued
(VII)
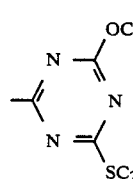
| R | Q | (substituent) |
|---|---|---|
| —CF₃ | O |  |
| —CF₃ | O | 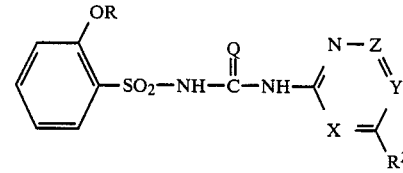 |
| —CF₃ | O | 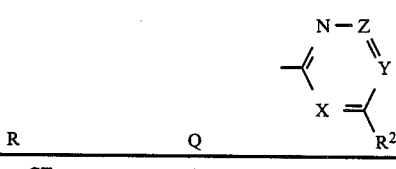 |
| —CF₃ | O | 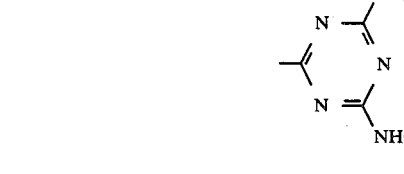 |
| —CF₃ | O | 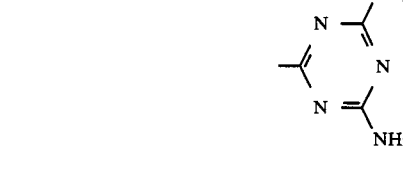 |
| —CF₃ | O | 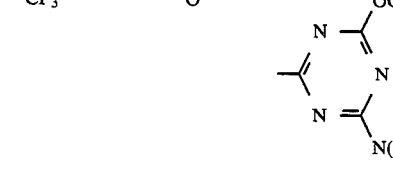 |
| —CF₃ | O | 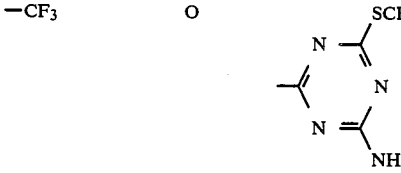 |

TABLE 3-continued
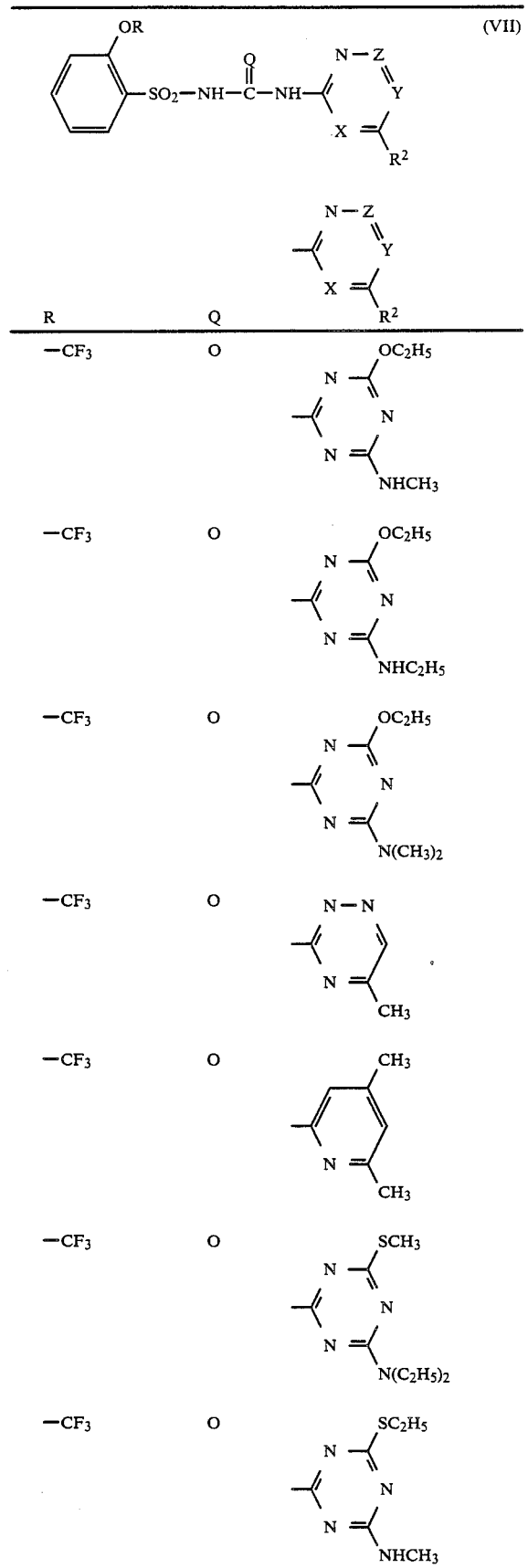
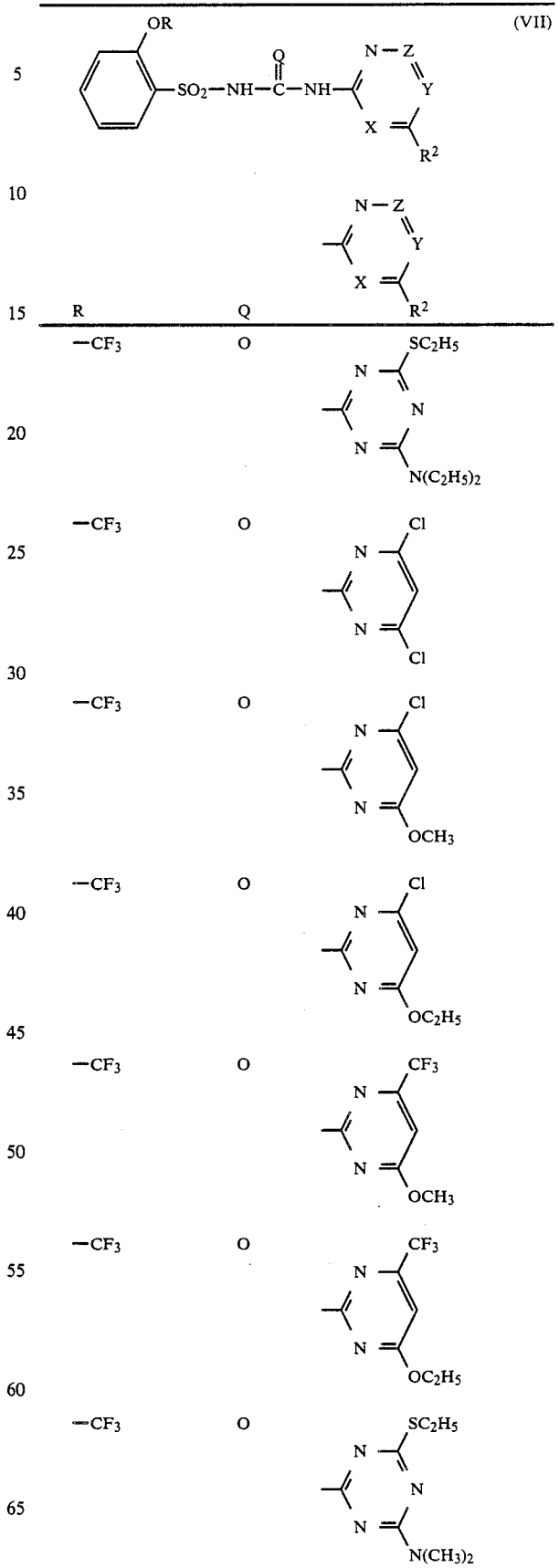

TABLE 3-continued

Structure (VII):

OR-phenyl-SO₂-NH-C(=Q)-NH- connected to heterocycle with N=Z, X, Y, R² substituents Heterocycle template:

```
    N=Z
   /   \
  —     Y
   \   /
    X
    |
    R²
```

| R | Q | heterocycle |
|---|---|---|
| —CF₃ | O | pyrazine with 3,6-di-CH₃ (N—N ring, CH₃, CH₃) |
| —CF₃ | O | pyrimidine with CH₃ and Cl |
| —CF₃ | O | pyrimidine with C₂H₅ and Cl |
| —CF₃ | O | pyrimidine with C₂H₅ and OCH₃ |
| —CHF₂ | O | pyrimidine with CH₃ and CH₃ |
| —CHF₂ | O | pyrimidine with CH₃ and OCH₃ |
| —CHF₂ | O | pyrimidine with OCH₃ and OCH₃ |
| —CHF₂ | O | pyrimidine with C₂H₅ |
| —CHF₂ | O | pyrimidine with OC₂H₅ and OC₂H₅ |
| —CHF₂ | O | triazine with OCH₃ and CH₃ |
| —CHF₂ | O | triazine with OC₂H₅ and CH₃ |
| —CHF₂ | O | pyrimidine with OCH₃ and OCH₃ |
| —CHF₂ | O | pyrimidine with CH₃ and CH₃ |
| —CHF₂ | O | pyrimidine with CH₃ |

TABLE 3-continued $$\text{(VII)}$$

Structure: 2-(OR)-C6H4-SO2-NH-C(=O)-NH-C(=N-Z)(Y)(X=C-R2)

Heterocycle:

(N=Z, Y, X=C-R2 ring)

| R | Q | heterocycle |
|---|---|---|
| —CHF₂ | O | N=C(CH₃)–N=C(CH₃), with N in ring (pyrazine: 2,5-dimethyl) |
| —CHF₂ | O | N=C(OCH₃)–N=C(OCH₃) (pyrazine) |
| —CHF₂ | O | N=C(OC₂H₅)–N=C(OC₂H₅) (pyrazine) |
| —CHF₂ | O | N=C(OC₂H₅)–N=C(OCH₃) (pyrazine) |
| —CHF₂ | O | N=C(OCHF₂)–CH=C(CH₃) (pyrimidine) |
| —CHF₂ | O | N=C(CH₃)–N=C(SC₂H₅) (pyrazine) |
| —CHF₂ | O | N=C(OCH₃)–N=C(SCH₃) (pyrazine) |
| —CHF₂ | O | N=C(OC₂H₅)–N=C(SCH₃) (pyrazine) |
| —CHF₂ | O | N=C(OCH₃)–N=C(SC₂H₅) (pyrazine) |
| —CHF₂ | O | N=C(CH₃)–N=C(SCH₃) (pyrazine) |
| —CHF₂ | O | N=C(CH₃)–N=C(N(CH₃)₂) (pyrazine) |
| —CHF₂ | O | N=C(CH₃)–N=C(N(C₂H₅)₂) (pyrazine) |
| —CHF₂ | O | N=C(OCH₃)–N=C(NHCH₃) (pyrazine) |
| —CHF₂ | O | N=C(OCH₃)–N=C(NHC₂H₅) (pyrazine) |

TABLE 3-continued
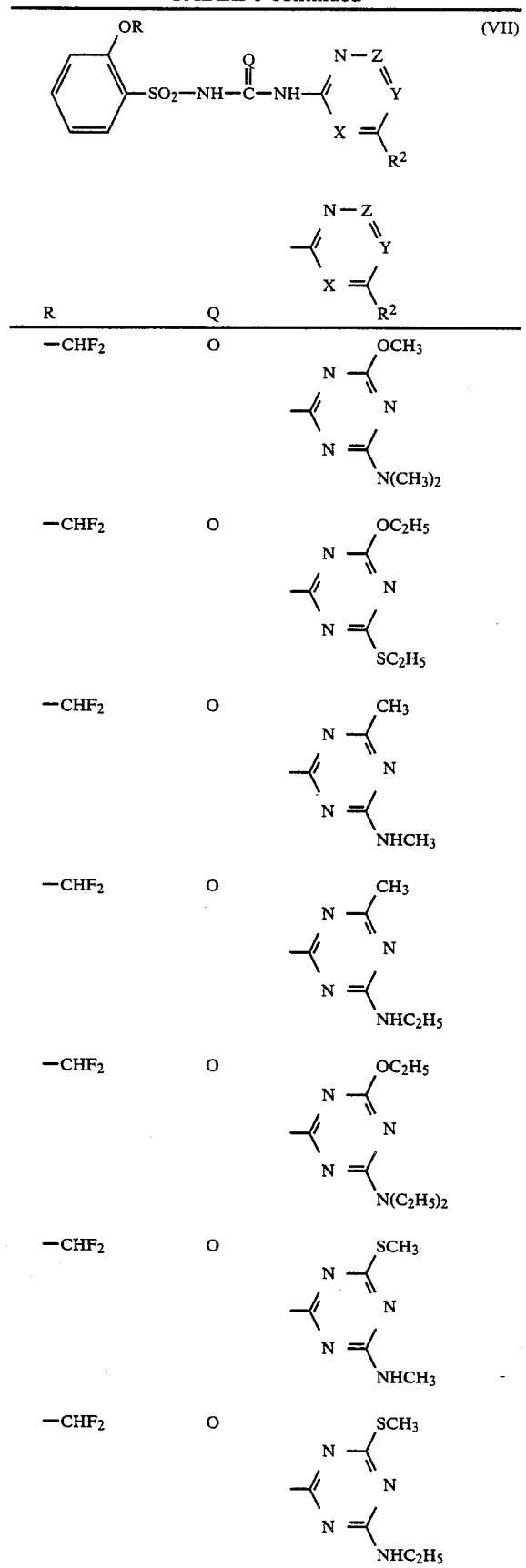
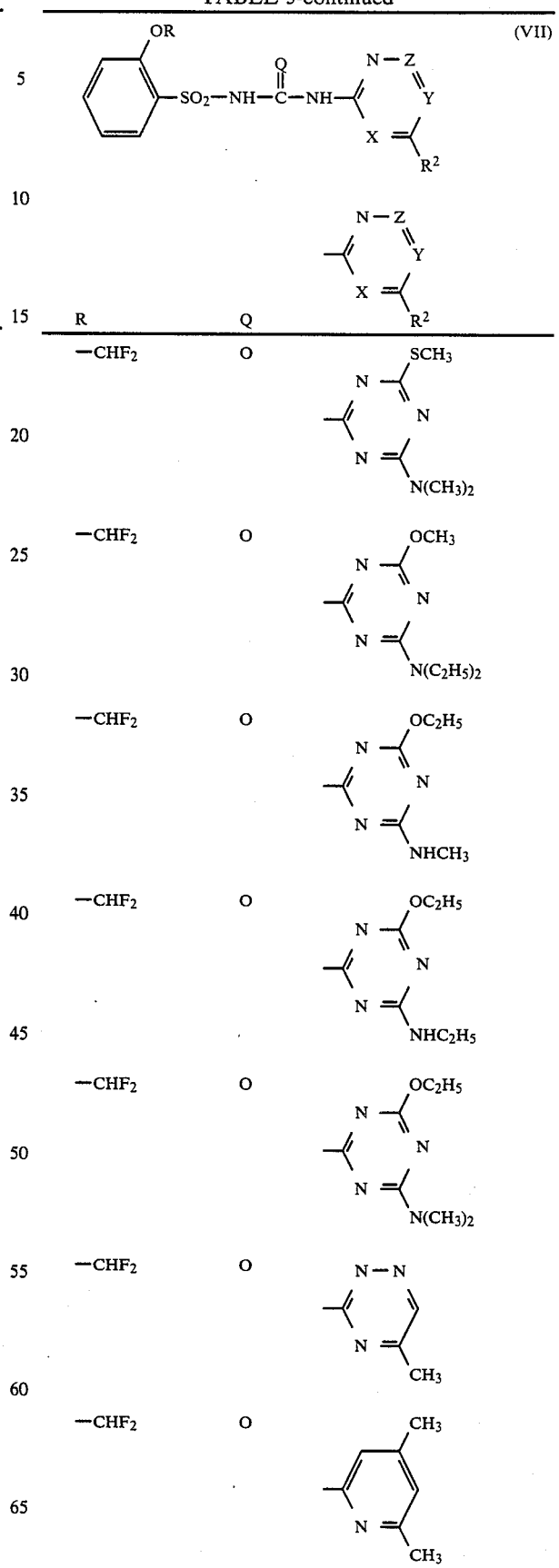

TABLE 3-continued
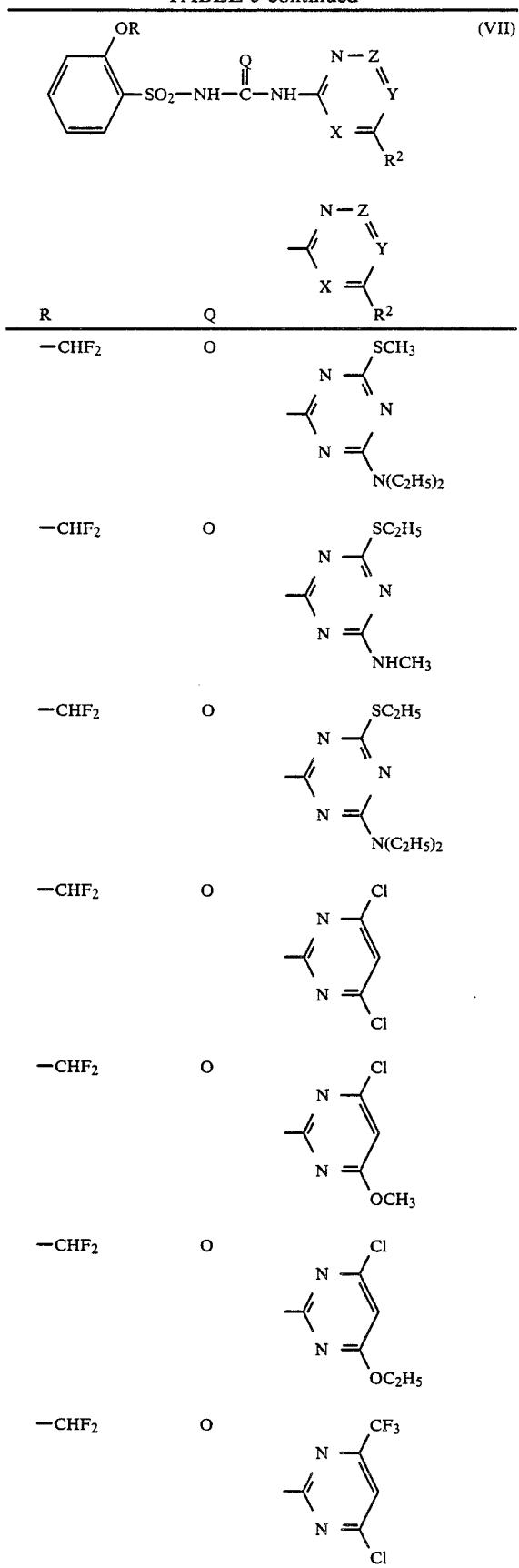
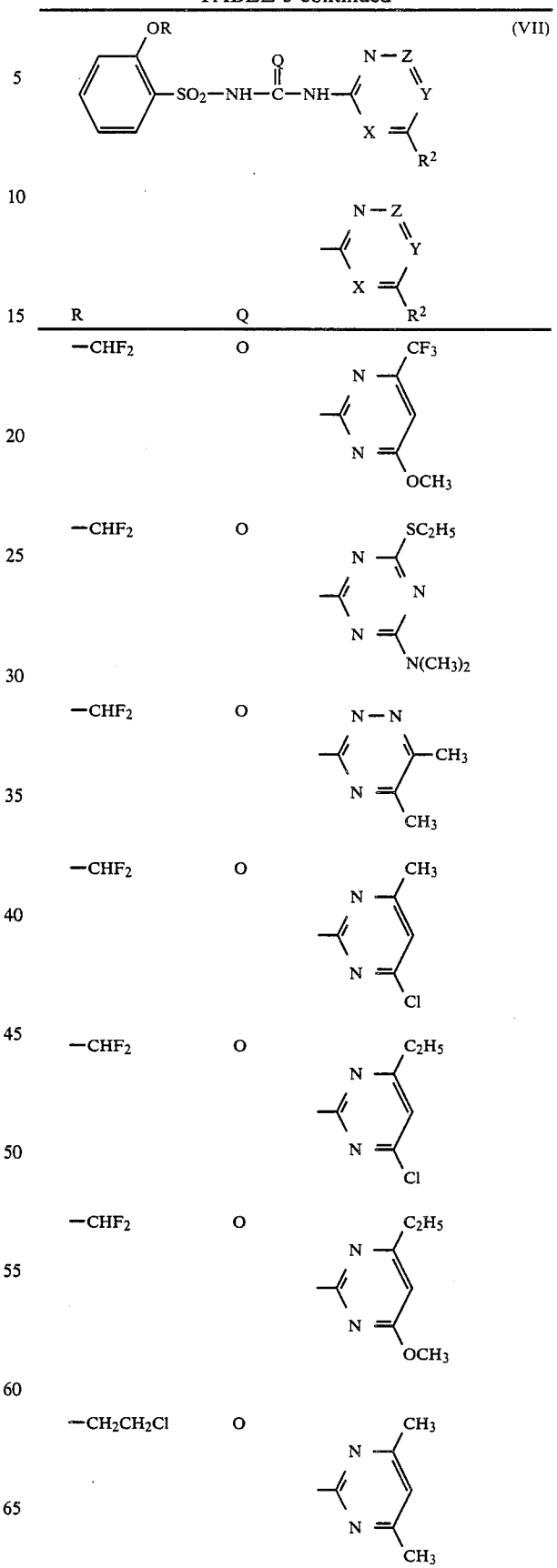

TABLE 3-continued $$\text{(VII)}$$

Structure: 2-(OR)-C$_6$H$_4$-SO$_2$-NH-C(=Q)-NH- heterocycle with N=Z, X, Y, R² substituents

| R | Q | heterocycle (R²/X/Y/Z) |
|---|---|---|
| —CH$_2$CH$_2$Cl | O | pyrimidine: 4-CH$_3$, 6-OCH$_3$ |
| —CH$_2$CH$_2$Cl | O | pyrimidine: 4-OCH$_3$, 6-OCH$_3$ |
| —CH$_2$CH$_2$Cl | O | pyrimidine: 4-C$_2$H$_5$ |
| —CH$_2$CH$_2$Cl | O | pyrimidine: 4-OC$_2$H$_5$, 6-OC$_2$H$_5$ |
| —CH$_2$CH$_2$Cl | O | triazine: OCH$_3$, CH$_3$ |
| —CH$_2$CH$_2$Cl | O | triazine: OC$_2$H$_5$, CH$_3$ |
| —CH$_2$CH$_2$Cl | O | pyrimidine: OCH$_3$, OCH$_3$ |
| —CH$_2$CH$_2$Cl | O | pyrimidine: CH$_3$, CH$_3$ |
| —CH$_2$CH$_2$Cl | O | pyrimidine: CH$_3$ |
| —CH$_2$CH$_2$Cl | O | pyrazine: CH$_3$, CH$_3$ |
| —CH$_2$CH$_2$Cl | O | triazine: OCH$_3$, OCH$_3$ |
| —CH$_2$CH$_2$Cl | O | triazine: OC$_2$H$_5$, OC$_2$H$_5$ |
| —CH$_2$CH$_2$Cl | O | triazine: OC$_2$H$_5$, OCH$_3$ |
| —CH$_2$CH$_2$Cl | O | pyrimidine: OCHF$_2$, CH$_3$ |

TABLE 3-continued $$\text{(VII)}$$

Structure: 2-(OR)-C6H4-SO2-NH-C(=Q)-NH- attached to a 6-membered ring containing N=Z, Y, X positions with R² substituent.

| R | Q | Ring substituents |
|---|---|---|
| —CH₂CH₂Cl | O | N=Z: CH₃ (top); ring with N, N; R²: SC₂H₅ |
| —CH₂CH₂Cl | O | N=Z: OCH₃; ring with N, N; R²: SCH₃ |
| —CH₂CH₂Cl | O | N=Z: OC₂H₅; ring with N, N; R²: SCH₃ |
| —CH₂CH₂Cl | O | N=Z: OCH₃; ring with N, N; R²: SC₂H₅ |
| —CF₂CHF₂ | O | N=Z: OCH₃; ring with N, N; R²: OCH₃ |
| —CH₂CH₂Cl | O | N=Z: CH₃; ring with N, N; R²: SCH₃ |
| —CH₂CH₂Cl | O | N=Z: CH₃; ring with N, N; R²: N(CH₃)₂ |
| —CH₂CH₂Cl | O | N=Z: CH₃; ring with N, N; R²: N(C₂H₅)₂ |
| —CH₂CH₂Cl | O | N=Z: OCH₃; ring with N, N; R²: NHCH₃ |
| —CH₂CH₂Cl | O | N=Z: OCH₃; ring with N, N; R²: NHC₂H₅ |
| —CH₂CH₂Cl | O | N=Z: OCH₃; ring with N, N; R²: N(CH₃)₂ |
| —CF₂CHF₂ | O | N=Z: CH₃; ring with N, N; R²: OCH₃ |
| —CH₂CH₂Cl | O | N=Z: OC₂H₅; ring with N, N; R²: SC₂H₅ |
| —CH₂CH₂Cl | O | N=Z: CH₃; ring with N, N; R²: NHCH₃ |

TABLE 3-continued $$\text{(VII)}$$

Structure: 2-(OR)-C6H4-SO2-NH-C(Q)-NH-[heterocycle with N-Z, X, Y, R²]

| R | Q | heterocycle (N—Z, X, Y, R²) |
|---|---|---|
| —CH₂CH₂Cl | O | triazine: R²=CH₃, with N, NHC₂H₅ |
| —CH₂CH₂Cl | O | triazine: R²=OC₂H₅, with N, N(C₂H₅)₂ |
| —CH₂CH₂Cl | O | triazine: R²=SCH₃, with N, NHCH₃ |
| —CH₂CH₂Cl | O | triazine: R²=SCH₃, with N, NHC₂H₅ |
| —CH₂CH₂Cl | O | triazine: R²=SCH₃, with N, N(CH₃)₂ |
| —CH₂CH₂Cl | O | triazine: R²=OCH₃, with N, N(C₂H₅)₂ |
| —CH₂CH₂Cl | O | triazine: R²=OC₂H₅, with N, NHCH₃ |
| —CH₂CH₂Cl | O | triazine: R²=OC₂H₅, with N, NHC₂H₅ |
| —CH₂CH₂Cl | O | triazine: R²=OC₂H₅, with N, N(CH₃)₂ |
| —CH₂CH₂Cl | O | triazine (N—N): with CH₃ |
| —CH₂CH₂Cl | O | pyridine: 4-CH₃, 6-CH₃ |
| —CH₂CH₂Cl | O | triazine: R²=SCH₃, with N, N(C₂H₅)₂ |
| —CH₂CH₂Cl | O | triazine: R²=SC₂H₅, with N, NHCH₃ |
| —CH₂CH₂Cl | O | triazine: R²=SC₂H₅, with N, N(C₂H₅)₂ |

TABLE 3-continued $$\text{(VII)}$$

Structure: 2-(OR)-C6H4-SO2-NH-C(=Q)-NH- attached to a heterocycle of form:

N=Z, Y, X, R² ring with Q substituent.

| R | Q | ring (N—Z, Y, X, R²) |
|---|---|---|
| —CH₂CH₂Cl | O | pyrimidine: 4-Cl, 6-Cl |
| —CH₂CH₂Cl | O | pyrimidine: 4-Cl, 6-OCH₃ |
| —CH₂CH₂Cl | O | pyrimidine: 4-Cl, 6-OC₂H₅ |
| —CH₂CH₂Cl | O | pyrimidine: 4-CF₃, 6-Cl |
| —CH₂CH₂Cl | O | pyrimidine: 4-CF₃, 6-OCH₃ |
| —CH₂CH₂Cl | O | pyrimidine: 4-SC₂H₅, 6-N(CH₃)₂ |
| —CH₂CH₂Cl | O | triazine: 4-CH₃, 6-CH₃ (N—N) |
| —CH₂CH₂Cl | O | pyrimidine: 4-CH₃, 6-Cl |
| —CH₂CH₂Cl | O | pyrimidine: 4-C₂H₅, 6-Cl |
| —CH₂CH₂Cl | O | pyrimidine: 4-C₂H₅, 6-OCH₃ |
| —CF₂CHF₂ | O | pyrimidine: 4-CH₃, 6-OCH₃ |
| —CF₂CHF₂ | O | pyrimidine: 4-OCH₃, 6-OCH₃ |
| —CF₃ | S | pyrimidine: 4-CH₃, 6-CH₃ |
| —CF₃ | S | pyrimidine: 4-CH₃, 6-OCH₃ |

TABLE 3-continued (VII)

Structure: Ar(OR)(SO₂—NH—C(=O)—NH—C(=N–Z)(X)(Y)(R²)) with heterocycle:

N—Z, Y, X, R² heterocyclic substituent

| R | Q | heterocycle (R², X, Y, Z positions) |
|---|---|---|
| —CF₃ | S | pyrimidine: 4-OCH₃, 6-OCH₃ |
| —CF₃ | S | pyrimidine: 4-C₂H₅ |
| —CF₃ | S | pyrimidine: 4-OC₂H₅, 6-OC₂H₅ |
| —CF₃ | S | triazine: 4-OCH₃, 6-CH₃ |
| —CF₃ | S | triazine: 4-OC₂H₅, 6-CH₃ |
| —CF₃ | S | pyrimidine: 4-OCH₃, 6-OCH₃ |
| —CF₃ | S | pyrimidine: 4-CH₃, 6-CH₃ |
| —CF₃ | S | pyrimidine: 4-CH₃ |
| —CF₃ | S | triazine: 4-CH₃, 6-CH₃ |
| —CF₃ | S | triazine: 4-OCH₃, 6-OCH₃ |
| —CF₃ | S | triazine: 4-OC₂H₅, 6-OC₂H₅ |
| —CF₃ | S | triazine: 4-OC₂H₅, 6-OCH₃ |
| —CF₃ | S | pyrimidine: 4-OCHF₂, 6-CH₃ |
| —CF₃ | S | triazine: 4-CH₃, 6-SC₂H₅ |

TABLE 3-continued $$\text{(VII)}$$

Structure: 2-OR-phenyl-SO$_2$-NH-C(=O)-NH-C(=N-Z)(X)-C(Y)=C(R$^2$), where the right portion is a ring with N-Z, Y, X, R$^2$.

Substituent group:

N=Z, Y, X, R$^2$ ring

| R | Q | R$^2$ ring substituent |
|---|---|---|
| —CF$_3$ | S | 2-OCH$_3$, 5-SCH$_3$ pyrimidine |
| —CF$_3$ | S | 2-OC$_2$H$_5$, 5-SCH$_3$ pyrimidine |
| —CF$_3$ | S | 2-OCH$_3$, 5-SC$_2$H$_5$ pyrimidine |
| —CF$_3$ | S | 2-CH$_3$, 5-SCH$_3$ pyrimidine |
| —CF$_3$ | S | 2-CH$_3$, 5-N(CH$_3$)$_2$ pyrimidine |
| —CF$_3$ | S | 2-CH$_3$, 5-N(C$_2$H$_5$)$_2$ pyrimidine |
| —CF$_3$ | S | 2-OCH$_3$, 5-NHCH$_3$ pyrimidine |
| —CF$_3$ | S | 2-OCH$_3$, 5-NHC$_2$H$_5$ pyrimidine |
| —CF$_3$ | S | 2-OCH$_3$, 5-N(CH$_3$)$_2$ pyrimidine |
| —CF$_3$ | S | 2-OC$_2$H$_5$, 5-SC$_2$H$_5$ pyrimidine |
| —CF$_3$ | S | 2-CH$_3$, 5-NHCH$_3$ pyrimidine |
| —CF$_3$ | S | 2-CH$_3$, 5-NHC$_2$H$_5$ pyrimidine |
| —CF$_3$ | S | 2-OC$_2$H$_5$, 5-N(C$_2$H$_5$)$_2$ pyrimidine |
| —CF$_3$ | S | 2-SCH$_3$, 5-NHCH$_3$ pyrimidine |

TABLE 3-continued

Structure (VII): 2-(OR)-phenyl-SO₂-NH-C(=O)-NH-C(=X)-N=Z-Y with R² substituent

| R | Q | Heterocycle |
|---|---|---|
| —CF₃ | S | triazine with SCH₃ and NHC₂H₅ |
| —CF₃ | S | triazine with SCH₃ and N(CH₃)₂ |
| —CF₃ | S | triazine with OCH₃ and N(C₂H₅)₂ |
| —CF₃ | S | triazine with OC₂H₅ and NHCH₃ |
| —CF₃ | S | triazine with OC₂H₅ and NHC₂H₅ |
| —CF₃ | S | triazine with OC₂H₅ and N(CH₃)₂ |
| —CF₃ | S | triazine with CH₃ |
| —CF₃ | S | pyridine with two CH₃ |
| —CF₃ | S | triazine with SCH₃ and N(C₂H₅)₂ |
| —CF₃ | S | triazine with SC₂H₅ and NHCH₃ |
| —CF₃ | S | triazine with SC₂H₅ and N(C₂H₅)₂ |
| —CF₃ | S | pyrimidine with two Cl |
| —CF₃ | S | pyrimidine with Cl and OCH₃ |
| —CF₃ | S | pyrimidine with Cl and OC₂H₅ |

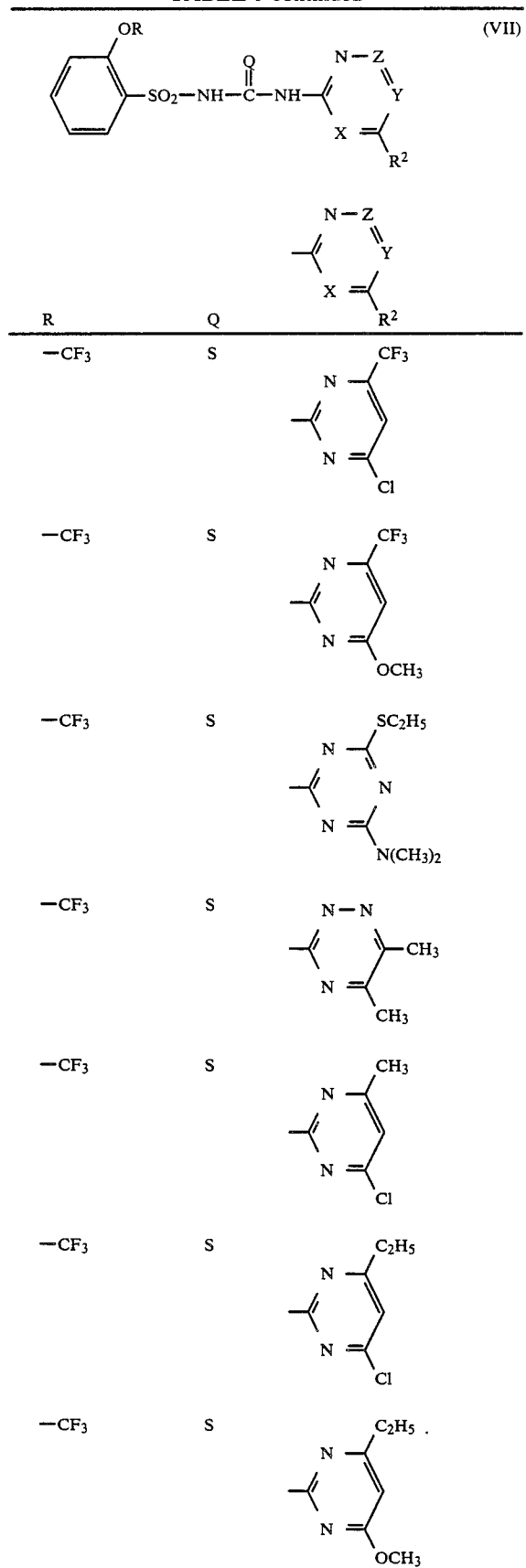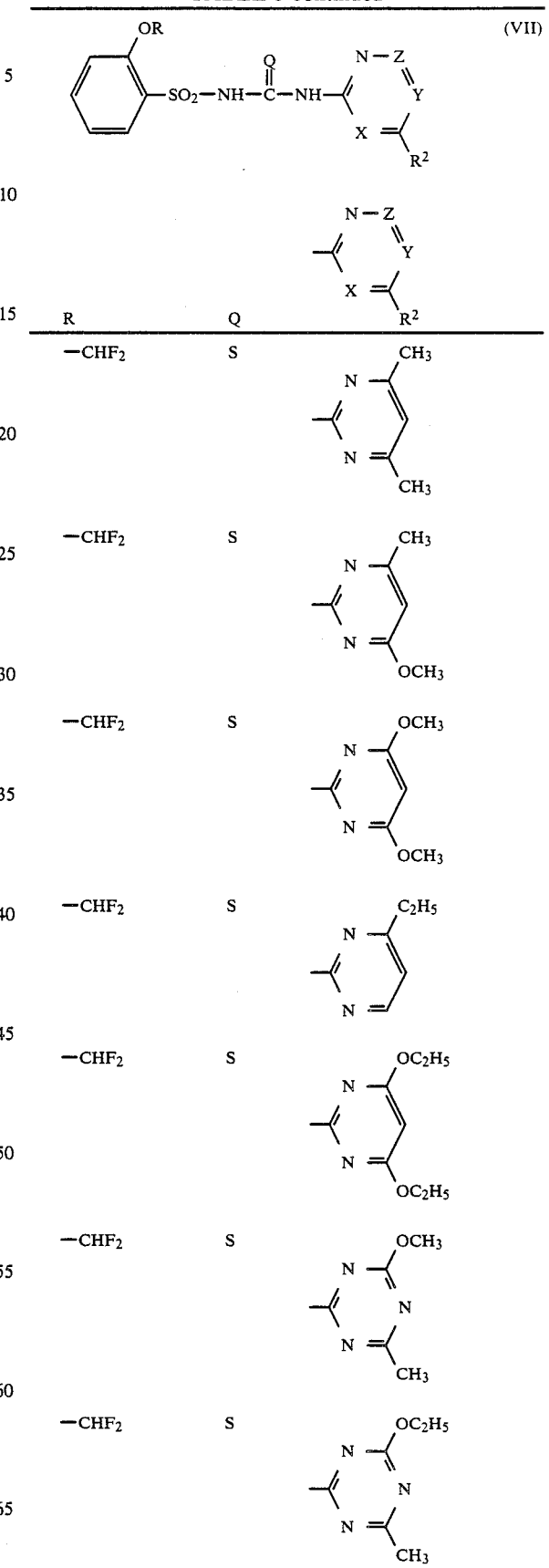

TABLE 3-continued $$\text{(VII)}$$

Structure: 2-OR-phenyl-SO$_2$-NH-C(=O)-NH-C(=N-Z)(X)-... with heterocycle containing N-Z, Y, X, R$^2$

| R | Q | R$^2$ heterocycle |
|---|---|---|
| —CHF$_2$ | S | pyrimidine with OCH$_3$, OCH$_3$ |
| —CHF$_2$ | S | pyrimidine with CH$_3$, CH$_3$ |
| —CHF$_2$ | S | pyrimidine with CH$_3$ (4-position) |
| —CHF$_2$ | S | pyrazine with CH$_3$, CH$_3$ |
| —CHF$_2$ | S | triazine with OCH$_3$, OCH$_3$ |
| —CHF$_2$ | S | triazine with OC$_2$H$_5$, OC$_2$H$_5$ |
| —CHF$_2$ | S | triazine with OC$_2$H$_5$, OCH$_3$ |
| —CHF$_2$ | S | triazine with OCHF$_2$, CH$_3$ |
| —CHF$_2$ | S | triazine with CH$_3$, SC$_2$H$_5$ |
| —CHF$_2$ | S | triazine with OCH$_3$, SCH$_3$ |
| —CHF$_2$ | S | triazine with OC$_2$H$_5$, SCH$_3$ |
| —CHF$_2$ | S | triazine with OCH$_3$, SC$_2$H$_5$ |
| —CHF$_2$ | S | triazine with CH$_3$, SCH$_3$ |
| —CHF$_2$ | S | triazine with CH$_3$, N(CH$_3$)$_2$ |

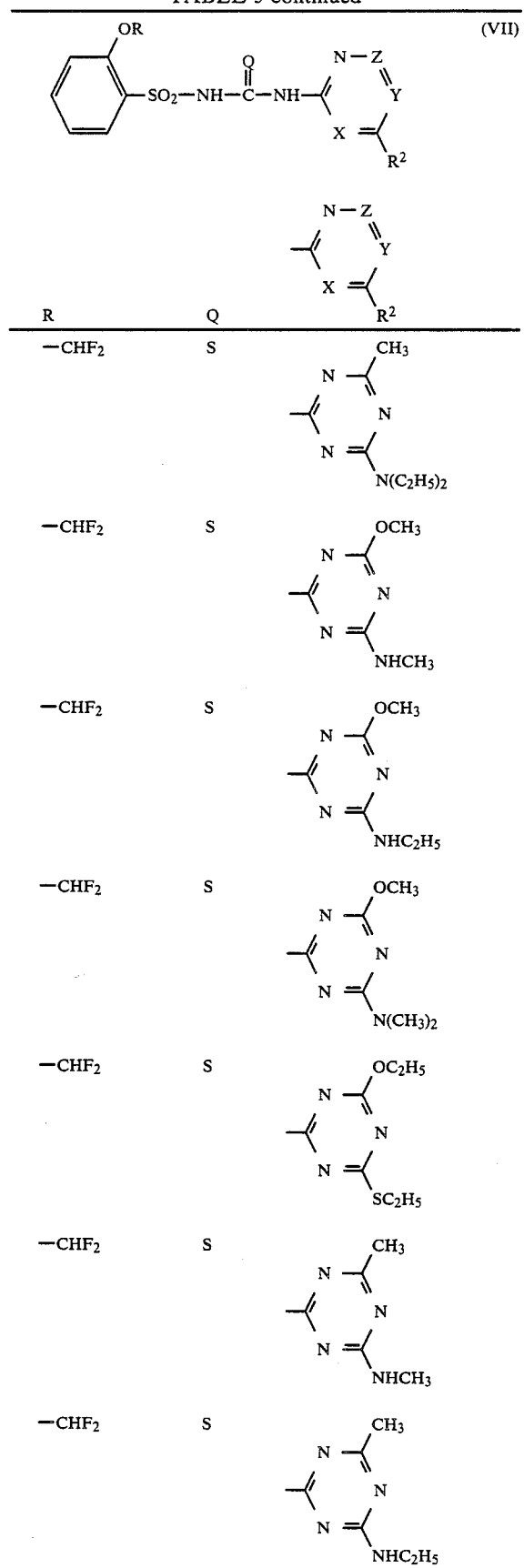
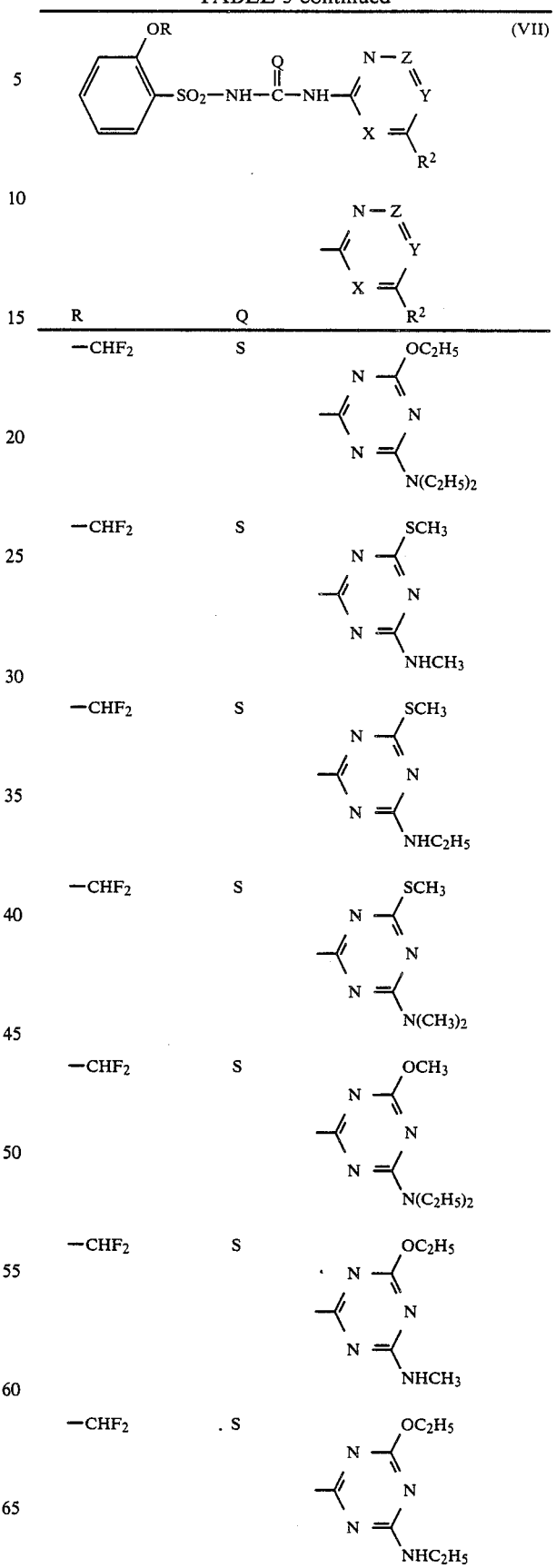

TABLE 3-continued

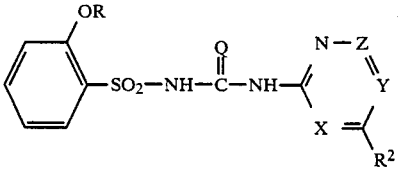
(VII)

| R | Q | (substituent) |
|---|---|---|
| —CHF$_2$ | S | pyrimidine with OC$_2$H$_5$ and N(CH$_3$)$_2$ |
| —CHF$_2$ | S | triazine with CH$_3$ |
| —CHF$_2$ | S | pyridine with CH$_3$, CH$_3$ |
| —CHF$_2$ | S | pyrimidine with SCH$_3$ and N(C$_2$H$_5$)$_2$ |
| —CHF$_2$ | S | pyrimidine with SC$_2$H$_5$ and NHCH$_3$ |
| —CHF$_2$ | S | pyrimidine with SC$_2$H$_5$ and N(C$_2$H$_5$)$_2$ |
| —CHF$_2$ | S | pyrimidine with Cl and Cl |
| —CHF$_2$ | S | pyrimidine with Cl and OCH$_3$ |
| —CHF$_2$ | S | pyrimidine with Cl and OC$_2$H$_5$ |
| —CHF$_2$ | S | pyrimidine with CF$_3$ and Cl |
| —CHF$_2$ | S | pyrimidine with CF$_3$ and OCH$_3$ |
| —CHF$_2$ | S | pyrimidine with SC$_2$H$_5$ and N(CH$_3$)$_2$ |
| —CHF$_2$ | S | triazine with CH$_3$, CH$_3$ |
| —CHF$_2$ | S | pyrimidine with CH$_3$ and Cl |

TABLE 3-continued $$\text{(VII)}$$

Structure: 2-OR-phenyl-SO$_2$-NH-C(=O)-NH-C(Q)=N-Z-Y-X(R$^2$) heterocycle

| R | Q | heterocycle |
|---|---|---|
| —CHF$_2$ | S | 4-C$_2$H$_5$-6-Cl-pyrimidin-2-yl |
| —CHF$_2$ | S | 4-C$_2$H$_5$-6-OCH$_3$-pyrimidin-2-yl |
| —CH$_2$CH$_2$Cl | S | 4,6-di-CH$_3$-pyrimidin-2-yl |
| —CH$_2$CH$_2$Cl | S | 4-CH$_3$-6-OCH$_3$-pyrimidin-2-yl |
| —CH$_2$CH$_2$Cl | S | 4,6-di-OCH$_3$-pyrimidin-2-yl |
| —CH$_2$CH$_2$Cl | S | 4-C$_2$H$_5$-pyrimidin-2-yl |
| —CH$_2$CH$_2$Cl | S | 4,6-di-OC$_2$H$_5$-pyrimidin-2-yl |
| —CH$_2$CH$_2$Cl | S | 4-OCH$_3$-6-CH$_3$-triazin-2-yl |
| —CH$_2$CH$_2$Cl | S | 4-OC$_2$H$_5$-6-CH$_3$-triazin-2-yl |
| —CH$_2$CH$_2$Cl | S | 4,6-di-OCH$_3$-pyrimidin-2-yl |
| —CH$_2$CH$_2$Cl | S | 4,6-di-CH$_3$-triazin-2-yl |
| —CH$_2$CH$_2$Cl | S | 4-CH$_3$-pyrimidin-2-yl |
| —CH$_2$CH$_2$Cl | S | 4,6-di-CH$_3$-triazin-2-yl |
| —CH$_2$CH$_2$Cl | S | 4,6-di-OCH$_3$-triazin-2-yl |

TABLE 3-continued (VII) Structure: Ar(OR)-SO₂-NH-C(=Q)-NH-[heterocycle with N=Z, X, Y, R²]

Heterocycle template:
```
    N—Z
   /   \
  —     Y
   \   /
    X
    |
    R²
```

| R | Q | R² (heterocycle substituents) |
|---|---|---|
| —CH₂CH₂Cl | S | N=Z: OC₂H₅ / OC₂H₅ (pyrimidine) |
| —CH₂CH₂Cl | S | OC₂H₅ / OCH₃ |
| —CH₂CH₂Cl | S | OCHF₂ / CH₃ |
| —CH₂CH₂Cl | S | CH₃ / SC₂H₅ |
| —CH₂CH₂Cl | S | OCH₃ / SCH₃ |
| —CH₂CH₂Cl | S | OC₂H₅ / SCH₃ |
| —CH₂CH₂Cl | S | OCH₃ / SC₂H₅ |
| —CH₂CH₂Cl | S | CH₃ / SCH₃ |
| —CH₂CH₂Cl | S | CH₃ / N(CH₃)₂ |
| —CH₂CH₂Cl | S | CH₃ / N(C₂H₅)₂ |
| —CH₂CH₂Cl | S | OCH₃ / NHCH₃ |
| —CH₂CH₂Cl | S | OCH₃ / NHC₂H₅ |
| —CH₂CH₂Cl | S | OCH₃ / N(CH₃)₂ |
| —CH₂CH₂Cl | S | OC₂H₅ / SC₂H₅ |

TABLE 3-continued

Structure (VII):
Ar(OR)-SO₂-NH-C(O)-NH-Q-[heterocycle with N-Z, X, Y, R²]

| R | Q | R² (heterocycle) |
|---|---|---|
| —CH₂CH₂Cl | S | pyrimidine, CH₃ / NHCH₃ |
| —CH₂CH₂Cl | S | pyrimidine, CH₃ / NHC₂H₅ |
| —CH₂CH₂Cl | S | pyrimidine, OC₂H₅ / N(C₂H₅)₂ |
| —CH₂CH₂Cl | S | pyrimidine, SCH₃ / NHCH₃ |
| —CH₂CH₂Cl | S | pyrimidine, SCH₃ / NHC₂H₅ |
| —CH₂CH₂Cl | S | pyrimidine, SCH₃ / N(CH₃)₂ |
| —CH₂CH₂Cl | S | pyrimidine, OCH₃ / N(C₂H₅)₂ |
| —CH₂CH₂Cl | S | pyrimidine, OC₂H₅ / NHCH₃ |
| —CH₂CH₂Cl | S | pyrimidine, OC₂H₅ / NHC₂H₅ |
| —CH₂CH₂Cl | S | pyrimidine, OC₂H₅ / N(CH₃)₂ |
| —CH₂CH₂Cl | S | triazine, CH₃ |
| —CH₂CH₂Cl | S | pyridine, CH₃ / CH₃ |
| —CH₂CH₂Cl | S | pyrimidine, SCH₃ / N(C₂H₅)₂ |
| —CH₂CH₂Cl | S | pyrimidine, SC₂H₅ / NHCH₃ |

TABLE 3-continued (VII) Structure: Ar(OR)-SO₂-NH-C(O)-NH-C(=N-Z,X,Y,R²)

| R | Q | (ring substituents) |
|---|---|---|
| —CH₂CH₂Cl | S | pyrimidine: 4-SC₂H₅, 6-N(C₂H₅)₂ |
| —CH₂CH₂Cl | S | pyrimidine: 4-Cl, 6-Cl |
| —CH₂CH₂Cl | S | pyrimidine: 4-Cl, 6-OCH₃ |
| —CH₂CH₂Cl | S | pyrimidine: 4-Cl, 6-OC₂H₅ |
| —CH₂CH₂Cl | S | pyrimidine: 4-CF₃, 6-Cl |
| —CH₂CH₂Cl | S | pyrimidine: 4-CF₃, 6-OCH₃ |
| —CH₂CH₂Cl | S | pyrimidine: 4-SC₂H₅, 6-N(CH₃)₂ |
| —CH₂CH₂Cl | S | triazine: 4-CH₃, 6-CH₃ |
| —CH₂CH₂Cl | S | pyrimidine: 4-CH₃, 6-Cl |
| —CH₂CH₂Cl | S | pyrimidine: 4-C₂H₅, 6-Cl |
| —CH₂CH₂Cl | S | pyrimidine: 4-C₂H₅, 6-OCH₃ |
| —CF₂CHF₂ | S | pyrimidine: 4-CH₃, 6-OCH₃ |
| —CF₂CHF₂ | S | pyrimidine: 4-OCH₃, 6-OCH₃ |
| —CF₂CHF₂ | S | triazine: 4-CH₃, 6-OCH₃ |

TABLE 3-continued (VII)

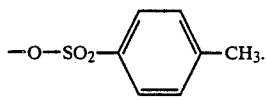

| R | Q | R² |
|---|---|---|
| —CF₂CHF₂ | S | OCH₃ ![N-Z/Y structure with OCH₃] |
| | | ![triazine with N, N, OCH₃] |

The compounds of the formula (VII) are known and/or can be prepared by known methods (compare, for example, European Pat. Nos. A-44,808, 44,809 and European Pat. No. A-173,312).

Formula (VIII) provides a general definition of the compounds also to be used as starting substances in process (d) according to the invention. In this formula (VIII), $R^1$ preferably or particularly represents those radicals which have already been mentioned as preferred or as particularly preferred for this substituent in connection with the description of the substances of the formula (I) according to the invention. W in formula (VIII) represents a nucleophilic leaving group, preferably chloride, bromide, iodide, —O—SO₂—OCH₃, —O—SO₂CH₃ or —O—SO₂—⟨phenyl⟩—CH₃.

Examples which may be mentioned of the compounds of the formula (VIII) are: methyl, ethyl, n-propyl, i-propyl, n-butyl, i-butyl, benzyl, allyl and propargyl chloride, bromide and iodide, as well as dimethyl sulphate and methyl p-toluenesulphonate.

The compounds of the formula (VIII) are generally known compounds of organic chemistry.

Process (a) according to the invention for the preparation of the new compounds of the formula (I) is preferably carried out using diluents. Possible diluents here are virtually all the inert organic solvents. These include, preferably, aliphatic and aromatic, optionally halogenated, hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylene sulphone and hexamethylphosphoric acid triamide.

If appropriate, process (a) according to the invention is carried out in the presence of a catalyst. Catalysts include, in particular, aliphatic, aromatic or heterocyclic amines, such as triethylamine, N,N-dimethylaniline, pyridine, 2-methyl-5-ethyl-pyridine, 4-dimethylaminopyridine, diazabicyclooctane (DABCO), diazabicyclononene (DBN) and diazabicycloundecene (DBU).

The reaction temperatures can be varied within a substantial range in process (a) according to the invention. The reaction is in general carried out at temperatures between 0° C. and 150° C., preferably at temperatures between 20° C. and 100° C.

Process (a) according to the invention is in general carried out under normal pressure. However, it is also possible for the process to be carried out under increased or reduced pressure.

For carrying out process (a) according to the invention, in general 1.0 to 3.0 mols, preferably 1.0 to 2.0 mols, of 2-halogenoalkoxy-benzenesulphonyl iso(thio)-cyanate of the formula (II) are employed per mol of heteroarylamine of the formula (III).

The starting substances of the formulae (II) and (III), and if appropriate the catalyst and the diluent, are in general brought together at room temperature or with gentle external cooling and the reaction mixture is stirred, if appropriate at elevated temperature, until the reaction has ended.

The new compounds of the formula (I) are worked up and isolated by customary methods: if the compounds of the formula (I) are obtained as crystals, they are isolated by filtration with suction. Otherwise—if appropriate after concentration—water and an organic solvent which is virtually water-immiscible are added and, after thorough shaking, the organic phase is separated off, dried, filtered and evaporated, the products of the formula (I) remaining in the residue.

The preparation process described above under (b) for the compounds of the formula (I) is preferably carried out in the presence of diluents. The same organic solvents as have been mentioned above in connection with the description of process (a) according to the invention are possible here.

Acid acceptors which can be employed in process (b) according to the invention are all the acid-binding agents which can usually be used for such reactions. Preferred suitable acid-binding agents are alkali metal hydroxides, such as, for example, sodium hydroxide and potassium hydroxide, alkaline earth metal hydroxides, such as, for example, calcium hydroxide, alkali metal carbonates and alcoholates, such as sodium carbonate and potassium carbonate and sodium methylate and ethylate and potassium methylate and ethylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures can be varied within a substantial range in process (b) according to the invention. The reaction is in general carried out at temperatures between —20° C. and +100° C., preferably at temperatures between 0° C. and 50° C.

Process (b) according to the invention is in general carried out under normal pressure. However, it also possible for the process of be carried out under is increased or reduced pressure.

For carrying out process (b) according to the invention, in general 1.0 to 1.5 mols, preferably 1.0 to 1.2 mols, of 2-halogenoalkoxy-benzenesulphonic acid amide of the formula (IV) are employed per mol of N-heteroarylurethane of the formula (V).

The starting substances of the formulae (IV) and (V), and if appropriate the acid acceptor and the diluent, are in general brought together at room temperature or with gentle external cooling and the reaction mixture is stirred, if appropriate at elevated temperature, until the reaction has ended. Working up and isolation of the new compounds of the formula (I) can be carried out by customary methods: in general—if appropriate after concentration—the mixture is stirred with water and if appropriate acidified with hydrochloric acid. If the compounds of the formula (I) are obtained here as crystals, they are filtered off with suction. Otherwise, the mixture is extracted with a solvent which is virtually water-immiscible, such as, for example, ethyl acetate or methylene chloride, and the organic phase is separated off, dried, filtered and concentrated, the products of the formula (I) remaining in the residue.

The preparation process described above under (c) for the compounds of the formula (I) is preferably carried out in the presence of diluents. The same organic solvents as have been mentioned above in connection with the description of process (a) according to the invention are possible here.

Process (c) according to the invention is preferably carried out in the presence of an acid acceptor. Possible acid acceptors here are the same inorganic acid-binding agents and organic bases as have been mentioned above in connection with the description of process (b) according to the invention.

The reaction temperatures can be varied within a substantial range in process (c) according to the invention. The reaction is in general carried out at temperatures between −20° C. and +100° C., preferably at temperatures between 0° C. and 50° C. Process (c) according to the invention is in general carried out under normal pressure. However, it is also possible to carry out the process under increased or reduced pressure.

For carrying out process (c) according to the invention, in general 1.0 to 1.5 mols, preferably 1.0 to 1.2 mols, of heteroarylamine of the formula (III) are employed per mol of N-(2-halogenoalkoxy-benzenesulphonyl)urethane of the formula (VI).

The reaction can be carried out and the mixture worked up in process (c) as described above for process (b).

Polar organic solvents can preferably be employed as diluents in carrying out process (d) according to the invention. Preferred possible solvents here are ketones, such as, for example, acetone, methyl ethyl ketone, methyl isopropyl ketone and methyl isobutyl ketone, and furthermore nitriles, and in addition amides, such as dimethylformamide, dimethylacetamide and N-methylpyrrolidone, as well as ethers, such as diethyl ether, dibutyl ether, glycol dimethyl ether, diglycol dimethyl ether, tetrahydrofuran and dioxane.

Strongly basic but weakly nucleophilic substances can preferably be employed as acid acceptors in carrying out process (d) according to the invention. Acid acceptors which are preferably suitable are alkali metal hydrides, such as, for example, sodium hydride and potassium hydride, alkaline earth metal hydrides, such as, for example, calcium hydride, alkali metal carbonates and alcoholates, such as sodium carbonate and potassium carbonate, sodium methylate and ethylate and potassium methylate and ethylate and potassium tert-butylate, and furthermore 1,5-diazabicyclo-[4,3,0]-non-5-ene (DBN),1,8-diazabicyclo-[5,4,0]-undec-7-ene (DBU) and 1,4-diazabicyclo-[2,2,2]-octane (DABCO).

The reaction temperature can be varied within a substantial range in process (d) according to the invention for the preparation of the new compounds of the formula (I). The reaction is in general carried out at temperatures between 0° C. and +100° C., preferably between 0° C. and 80° C. Process (d) according to the invention is in general carried out under normal pressure.

For carrying out process (d) according to the invention, the particular starting substances required are in general employed in approximately equimolar amounts. However, it is also possible for one of the two particular components employed to be used in a larger excess. The reactions are in general carried out in a suitable diluent in the presence of an acid acceptor, and the reaction mixture is stirred for several hours at the particular temperature required. Working up is in each case carried out by customary methods in process (d) according to the invention.

The compounds of the formula (I) can be converted into salts with metals or with basic organic nitrogen compounds by customary methods. For this, the compounds of the formula (I) are in general dispersed in inert solvents, such as are mentioned above for preparation processes (a) to (d), and reacted with approximately equimolar amounts of soluble metal compounds, such as, for example, sodium methylate, potassium ethylate or calcium hydroxide, or with basic organic nitrogen compounds, such as, for example, isopropylamine, 2-hydroxy-ethylamine, dibutylamine, triethylamine or N,N-dimethyl-benzylamine, and the mixture is stirred at room temperature.

If the salts are obtained here as crystals, they are isolated by filtration with suction. Otherwise, they are obtained in crystalline form after distilling off the solvents.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinocloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischeaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchrds, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, tht is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oil.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used for combating weeds, as mixtures with known herbicides, finished formulations or tank mixes being possible.

Possible components for the mixtures are known herbicides, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 2-chloro-N-{[4-methoxy-6-methyl-1,3,5-triazin-2-yl)-amino]carbonyl}-benzenesulphonamide, ethyl 2-{[(4-chloro-6-methoxy-2-pyrimidyl)aminocarbonyl-]aminosulphonyl}-benzoate, 2-ethylamino-6(1,1-dimethylethyl-amino)-4-methylthio-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, 5-(2-chloro-4-trifluoromethyl-phenoxy)-N-methylsulphonyl-2-nitrobenzamide, (2-ethoxy-1-methyl-2-oxo-ethyl)-5-(2-chloro-4-trifluoromethyl-phenoxy)-2-nitro-benzoate, methyl 2-[4-(2,4-dichlorophenoxy)-phenoxy]-propionate, 2-{4-[(3-chloro-5-trifluoromethyl-2-pyridinyl)oxy]-phenoxy}-propionic acid, the R-enantiomer of (trimethylsilyl)methyl 2-{4-[(3,5-dichloro-2-pyridinyl)oxy]-phenoxy}-propionate, 2,4-dichlorophenoxyacetic acid, 2-(2,4-dichlorophenoxy)-propionic acid, 4-chloro-2-methyl-phenoxyacetic acid, 2-(4-chloro-2-methyl-phenoxy)-propionic acid, 3,5-diiodo-4-hydroxy-benzonitrile, 3,5-dibromo-4-hydroxybenzonitrile, 2-[5-methyl-5-(1-methylethyl)-4-oxo-2-imidazolin-2-yl]-3-pyridinecarboxylic acid, 2-(1-ethoxymino-butylidene)-5-(2-ethylthiopropyl)-1,3-cyclohexanedione, [(4-amino-3,5-dichloro-6-fluoro-2-pyridyl)oxy]acetic acid and 3-isopropyl-2,1,3-benzothiadiazin-(4)-one-2,2-dioxide.

Surprisingly, some mixtures also show a synergistic action.

Mixtures with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

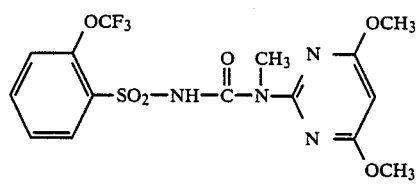

(Process variant (a))

A solution of 11.2 g (0.05 mol) of 2-trifluoromethoxy-benzenesulphonyl isocyanate in 50 ml of methylene chloride is added to a solution of 8.5 g (0.05 mol) of 4,6-dimethoxy-2-methylamino-pyrimidine in 50 ml of methylene chloride and the mixture is stirred at 20° C. for 12 hours. It is then concentrated and the residue is triturated with ether, filtered off with suction and dried.

2.6 g (12% of theory) of 3-(4,6-dimethoxy-pyrimidin-2-yl)-3-methyl-1-(2-trifluoromethoxy-benzenesulphonyl)urea of melting point 162° C. are obtained.

EXAMPLE 2

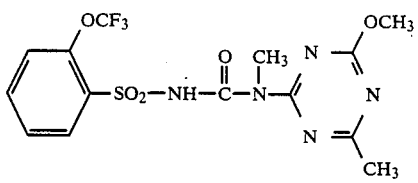

(Process variant (d))

4.1 g (0.01 mol) of 3-(4-methoxy-6-methyl-1,3,5-triazin-2-yl)-1-(2-trifluoromethoxy-benzenesulphonyl)-urea are taken up in 50 ml of tetrahydrofuran, and 2.4 b (0.02 mol) of potassium tert.-butylate and 1.7 g (0.018 mol) of dimethyl sulphate are added in succession. After the mixture has been stirred at 25° C. for 2 hours, it is concentrated, the residue is acidified with 10% strength hydrochloric acid and ethanol is added. The product obtained as crystals is filtered off with suction and dried.

3.0 g (71% of theory) of 3-methyl-3-(4-methoxy-6-methyl-1,3,5-triazin-2-yl)-1-(2-trifluoromethoxy-benzenesulphonyl)-urea are obtained as white crystals of melting point 162° C.

The compounds of the formula (I) listed in the following Table 4 can be prepared by the processes described by way of example in the preceding examples:

TABLE 4

| Example No. | R | O | R¹ | R² | Melting point/[°C.] |
|---|---|---|---|---|---|
| 3 | —CF₂CHF₂ | O | —CH₃ | (pyrimidine: CH₃, OCH₃) | 117 |
| 4 | —CF₃ | O | —CH₃ | (pyrimidine: OCH₃, Cl) | 173 |
| 5 | —CF₃ | O | —CH₃ | (pyrimidine: OC₂H₅, OC₂H₅) | 138 |

TABLE 4-continued $$\text{(I)}$$

| Example No. | R | R$^1$ | R$^2$ substituent | Melting point/[°C.] |
|---|---|---|---|---|
| 6 | —CF$_3$ | —CH$_3$ | 2-CH$_3$, 4-OC$_2$H$_5$, 6-Cl pyrimidinyl | 127 |
| 7 | —CF$_3$ | —CH$_3$ | 2-CH$_3$, 4-C$_2$H$_5$, 6-OCH$_3$ pyrimidinyl | 134 |
| 8 | —CF$_3$ | —CH$_3$ | 2-CH$_3$, 4-CH$_3$, 6-OC$_2$H$_5$ pyrimidinyl | 121 |
| 9 | —CF$_3$ | —CH$_3$ | 2-CH$_3$, 4-CH$_3$, 6-OCH$_3$ pyrimidinyl | 148 |
| 10 | —CF$_3$ | —CH$_3$ | 2-CH$_3$, 4-CH$_3$, 6-CH$_3$ pyrimidinyl | 169 |
| 11 | —CF$_3$ | —CH$_3$ | 2-CH$_3$, 4-CH$_3$, 6-Cl pyrimidinyl | |
| 12 | —CF$_3$ | —CH$_3$ | 2-CH$_3$, 4-C$_2$H$_5$, 6-Cl pyrimidinyl | |

TABLE 4-continued $$\text{(I)}$$

Structure (I): 2-OR-phenyl-SO₂—NH—C(=O)—N(R¹)—C(=N-Z-Y-...)(X-...R²), with pyrimidine ring shown:

| Example No. | R | O | R¹ | R² (pyrimidine substituents) | Melting point/[°C.] |
|---|---|---|---|---|---|
| 13 | —CF₃ | O | —CH₃ | 4-CF₃, 6-Cl, 2-(unsubst.) pyrimidine | |
| 14 | —CF₃ | O | —CH₃ | 4-CF₃, 6-OCH₃ pyrimidine | |
| 15 | —CF₃ | O | —CH₂CH=CH₂ | 4-CH₃, 6-OCH₃, 2-Me pyrimidine | 142 |
| 16 | —CF₂CHF₂ | O | —CH₃ | 4-CH₃, 6-Cl, 2-Me pyrimidine | |
| 17 | —CH₂CH₂Cl | O | —CH₃ | 4-C₂H₅, 6-OCH₃ pyrimidine | |
| 18 | —CHF₂ | O | —CH₃ | 4-OCH₃, 6-Cl pyrimidine | 156 |
| 19 | —CHF₂ | O | —CH₃ | 4-OC₂H₅, 6-Cl pyrimidine | 141 |

TABLE 4-continued

Structure (I):

Ar-OR, SO2-NH-C(=O)-N(R¹)-C(=N-Z-Y=X-R²) where the group attached is a 6-membered ring with N=Z, Y, X=, R²

| Example No. | R | O | R¹ | Heterocycle substituent | Melting point/[°C.] |
|---|---|---|---|---|---|
| 20 | —CHF₂ | O | —CH₃ | pyrimidine: 4-OCH₃, 6-OCH₃ | 140 |
| 21 | —CHF₂ | O | —CH₃ | pyrimidine: 4-OC₂H₅, 6-OC₂H₅ | 147 |
| 22 | —CHF₂ | O | —CH₃ | 1,3,5-triazine: 4-CH₃, 6-CH₃ | 142 |
| 23 | —CHF₂ | O | —CH₃ | 1,3,5-triazine: 4-OCH₃, 6-CH₃ | 156 |
| 24 | —CHF₂ | O | —CH₃ | 1,3,5-triazine: 4-OCH₃, 6-OCH₃ | — |
| 25 | —CHF₂ | O | —CH₃ | 1,3,5-triazine: 4-N(CH₃)₂, 6-CH₃ | — |
| 26 | —CHF₂ | S | —CH₃ | pyrimidine: 4-OCH₃, 6-OCH₃ | — |

TABLE 4-continued $$\text{(I)}$$

| Example No. | R | O | R¹ | R² | Melting point/[°C.] |
|---|---|---|---|---|---|
| 27 | —CHF₂ | S | —CH₃ | 4-OCH₃, 6-Cl pyrimidin-2-yl | |
| 28 | —CHF₂ | S | —CH₃ | 4-OC₂H₅, 6-Cl pyrimidin-2-yl | |
| 29 | —CHF₂ | S | —CH₃ | 4,6-di-OC₂H₅ pyrimidin-2-yl | |
| 30 | —CF₃ | O | —C₂H₅ | 4,6-di-OCH₃ pyrimidin-2-yl | |
| 31 | —CF₃ | O | —C₃H₇—n | 4,6-di-OCH₃ pyrimidin-2-yl | |
| 32 | —CF₃ | O | —CH₂—C₆H₅ | 4,6-di-OCH₃ pyrimidin-2-yl | 120 |
| 33 | —CF₃ | O | —CH₂—C₆H₅ | 4-CH₃, 6-OC₂H₅ pyrimidin-2-yl | |

TABLE 4-continued $$\text{(I)}$$

Structure: 2-(OR)-C$_6$H$_4$-SO$_2$-NH-C(=O)-N(R$^1$)-C(=N-Z)(X-...)(Y=...R$^2$ ring)

| Example No. | R | O | R$^1$ | R$^2$ ring | Melting point/[°C.] |
|---|---|---|---|---|---|
| 34 | —CH$_2$CH$_2$Cl | O | —CH$_3$ | 4-CH$_3$-6-OCH$_3$-pyrimidin-2-yl | |
| 35 | —CH$_2$CH$_2$Cl | S | —CH$_3$ | 4-C$_2$H$_5$-6-OCH$_3$-pyrimidin-2-yl | |
| 36 | —CH$_2$CH$_2$Cl | O | —CH$_3$ | 4-CH$_3$-6-Cl-pyrimidin-2-yl | |
| 37 | —CH$_2$CH$_2$Cl | O | —CH$_3$ | 4-OCH$_3$-6-OCH$_3$-pyrimidin-2-yl | |
| 38 | —CH$_2$CH$_2$Cl | O | —CH$_3$ | 4-OCH$_3$-6-Cl-pyrimidin-2-yl | |
| 39 | —CF$_2$—CHF$_2$ | O | —CH$_3$ | 4-OCH$_3$-6-OCH$_3$-pyrimidin-2-yl | |
| 40 | —CF$_2$—CHF$_2$ | O | —CH$_3$ | 4-Cl-6-OCH$_3$-pyrimidin-2-yl | |

TABLE 4-continued $$\text{(I)}$$

Structure: 2-(OR)-C$_6$H$_4$-SO$_2$-NH-C(=O)-N(R$^1$)-C(X=)(N=Z-Y-ring with R$^2$)

| Example No. | R | R$^1$ | R$^2$ group (heterocycle) | Melting point/[°C.] |
|---|---|---|---|---|
| 41 | —CF$_3$ | —CH$_3$ | pyrimidine with CH$_3$ and OCH$_3$ | |
| 42 | —CH$_2$CH$_2$Cl | —CH$_3$ | pyrimidine with Cl and C$_2$H$_5$ | |
| 43 | —CF$_3$ | —CH$_3$ | triazine with CH$_3$ and CH$_3$ | 120 |
| 44 | —CH$_2$CH$_2$Cl | —CH$_3$ | triazine with CH$_3$ and OCH$_3$ | |
| 45 | —CF$_2$CHF$_2$ | —CH$_3$ | triazine with CH$_3$ and OCH$_3$ | |
| 46 | —CH$_2$CH$_2$Cl | —CH$_3$ | triazine with OCH$_3$ and OCH$_3$ | |
| 47 | —CF$_2$CHF$_2$ | —CH$_3$ | triazine with OCH$_3$ and OCH$_3$ | |

TABLE 4-continued

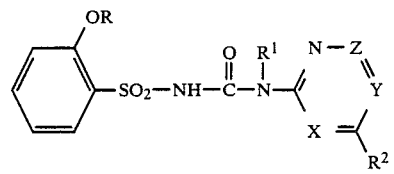
(I)

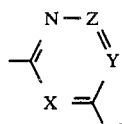

| Example No. | R | O | R¹ | R² | Melting point/[°C.] |
|---|---|---|---|---|---|
| 48 | —CF$_3$ | O | —CH$_3$ | ![structure with C$_2$H$_5$ and OCH$_3$ on triazine] | 143 |
| 49 | —CF$_3$ | O | —CH$_3$ | ![structure with CH$_3$ and OC$_2$H$_5$ on triazine] | |
| 50 | —CF$_3$ | O | —CH$_3$ | ![structure with C$_2$H$_5$ and OC$_2$H$_5$ on triazine] | |
| 51 | —CF$_3$ | O | —CH$_3$ | ![structure with OCH$_3$ and OC$_2$H$_5$ on triazine] | |
| 52 | —CF$_3$ | O | —CH$_3$ | ![structure with OC$_2$H$_5$ and OC$_2$H$_5$ on triazine] | 97 |
| 53 | —CF$_3$ | O | —CH$_3$ | ![structure with C$_2$H$_5$ and C$_2$H$_5$ on triazine] | |
| 54 | —CF$_3$ | O | —CH$_3$ | ![structure with OCH$_3$ and NHCH$_3$ on triazine] | |

TABLE 4-continued (I)

Structure: aryl with OR group, SO₂—NH—C(=O)—N(R¹)—C(=N—Z)—... with X=Y and R²

| Example No. | R | O | R¹ | (heterocycle) | Melting point/[°C.] |
|---|---|---|---|---|---|
| 55 | —CF₃ | O | —CH₃ | triazine: OCH₃, NHC₂H₅ | |
| 56 | —CF₃ | O | —CH₃ | triazine: OC₂H₅, NHCH₃ | |
| 57 | —CF₃ | O | —CH₃ | triazine: OC₂H₅, NHC₂H₅ | |
| 58 | —CF₃ | O | —CH₃ | triazine: OCH₃, N(CH₃)₂ | |
| 59 | —CF₃ | O | —CH₃ | triazine: CH₃, SCH₃ | |
| 60 | —CF₃ | O | —CH₃ | triazine: OCH₃, SCH₃ | |
| 61 | —CF₃ | O | —C₂H₅ | triazine: OCH₃, CH₃ | 107 |

TABLE 4-continued $$\text{(I)}$$

Structure: 2-(OR)-C$_6$H$_4$-SO$_2$-NH-C(=O)-N(R$^1$)-C(=N-Z=Y-X=CR$^2$ ring)

| Example No. | R | O | R$^1$ | R$^2$ (ring) | Melting point/[°C.] |
|---|---|---|---|---|---|
| 62 | —CF$_3$ | O | —C$_{12}$H$_{25}$ | 4,6-dimethylpyrimidin-2-yl | 100 |
| 63 | —CF$_3$ | O | —CH$_2$—C$_6$H$_5$ | 4-OCH$_3$-6-CH$_3$-pyrimidin-2-yl | 115 |
| 64 | —CF$_2$CHF$_2$ | O | —CH$_3$ | 4-CH$_3$-6-OC$_2$H$_5$-pyrimidin-2-yl | 136 |
| 65 | —CF$_2$CHF$_2$ | O | —CH$_3$ | 4,6-dimethylpyrimidin-2-yl | 105 |
| 66 | —CF$_3$ | O | —CH$_3$ | 4,6-dimethoxy-1,3,5-triazin-2-yl | 138 |
| 67 | CF$_3$ | O | —CH$_2$—CH=CH$_2$ | 4-CH$_3$-6-OCH$_3$-1,3,5-triazin-2-yl | 97 |
| 68 | CF$_3$ | O | C$_2$H$_5$ | 4,6-dimethoxy-1,3,5-triazin-2-yl | |

TABLE 4-continued

Structure (I): 2-(OR)-phenyl-SO$_2$-NH-C(=O)-N(R$^1$)-C(=N-Z-Y-R$^2$ / X ring system)

Heterocycle: 6-membered ring with N=Z, Y, X, R$^2$ substituent

| Example No. | R | R$^1$ | Heterocycle substituent | Melting point/[°C.] |
|---|---|---|---|---|
| 69 | CF$_3$ | —CH$_2$—CH=CH$_2$ | 2,6-bis(OCH$_3$)-1,3,5-triazin-4-yl | |
| 70 | CF$_3$ | —CH$_2$—C≡CH | 2,6-bis(OCH$_3$)-1,3,5-triazin-4-yl | |
| 71 | CF$_3$ | —CH(CH$_3$)$_2$ | 2,6-bis(OCH$_3$)-1,3,5-triazin-4-yl | |
| 72 | CF$_3$ | C$_2$H$_5$ | 2-CH$_3$-6-OCH$_3$-1,3,5-triazin-4-yl | |
| 73 | CF$_3$ | —CH$_2$—C≡CH | 2-CH$_3$-6-OCH$_3$-1,3,5-triazin-4-yl | |
| 74 | CF$_3$ | —CH(CH$_3$)$_2$ | 2-CH$_3$-6-OCH$_3$-1,3,5-triazin-4-yl | |
| 75 | CH$_2$CH$_2$Cl | CH$_3$ | 2,6-bis(OCH$_3$)-1,3,5-triazin-4-yl | |

TABLE 4-continued

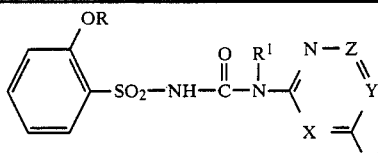

| Example No. | R | OR¹ | R² | Melting point/[°C.] |
|---|---|---|---|---|
| 76 | $CH_2CH_2Cl$ | $OCH_3$ | 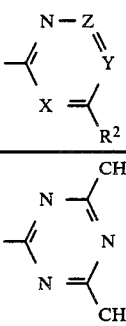 | |

EXAMPLE 77
Sodium salt of the product of Example 1

EXAMPLE 78
Sodium salt of the product of Example 4

EXAMPLE 79
Sodium salt of the product of Example 19

EXAMPLE 80
Sodium salt of the product of Example 20

EXAMPLE 81
Sodium salt of the product of Example 21

EXAMPLE 82
Sodium salt of the product of Example 32

The active compounds according to the invention not only display very powerful action against dicotyledonous weeds but are also very well tolerated by monocotyledonous crops such as, in particular, wheat, barley, rice and corn (maize), and in addition display virtually no persistence since they are decomposed very rapidly.

EXAMPLE A
Pre-emergence test
Solvent: 5 parts by weight of acetone
  Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient here to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the active compounds according to Preparation Examples 2, 22 and 66 exhibit a very good herbicidal activity; for instance they can be used for the selective combating of Abutilon, Datura, Sinapis and Stellaria in wheat cultures.

EXAMPLE B
Post-emergence test
Solvent: 5 parts by weight of acetone
  Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the active compounds according to Preparation Examples 2 and 66 exhibit a very good herbicidal activity. They can be used, for example, as selective herbicides for the combating of Datura, Galinsoga, Ipomoea, Matricaria, Stellaria and Lolium in wheat cultures.

It will be understood that the specification and examples are illustrative but not limitative of the present invention and that other embodiments within the spirit and scope of the invention will suggest themselves to those skilled in the art.

What is claimed is:

1. A compound selected from the group consisting of 3-methyl-3-(4-methoxy-6-methyl-1,3,5-triazin-2-yl)-1-(2-trifluoromethoxy-benzene-sulphonyl)-urea, 1-methyl-3-(4,6-dimethoxy-1,3,5-triazin-2-yl)-1-(2-trifluoromethoxy-benzene-sulphonyl)-urea or a salt thereof with a metal or basic organic nitrogen compound.

2. A compound according to claim 1, wherein such compound is 3-methyl-3-(4-methoxy-6-methyl-1,3,5-triazin-2-yl)-1-(2-trifluoromethoxy-benzene-sulphonyl)-urea of the formula

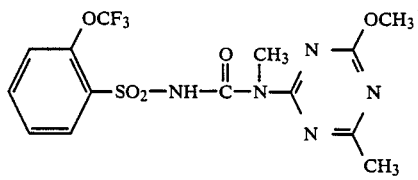

or a salt thereof with a metal or basic organic nitrogen compound.

3. A compound according to claim 1, wherein such compound is 3-methyl-3-(4,6-dimethoxy-1,3,5-triazin-2-yl)-(2-trifluoromethoxy-benzene-sulphonyl)-urea of the formula

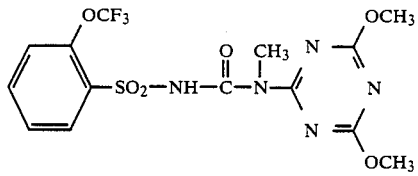

or a salt thereof with a metal or basic organic nitrogen compound.

4. A herbicidal composition comprising a herbicidally effective amount of a compound or salt according to claim 1.

5. A method of combating unwanted vegetation which comprises applying to such vegetation or to a locus from which it is desired to exclude such vegetation a herbicidally effective amount of a compound or salt according to claim 1.

6. The method according to claim 5 wherein such compound is 3-methyl-3-(4-methoxy-6-methyl-1,3,5-triazin-2-yl)-1-(2-trifluoromethoxy-benzene-sulphonyl)-urea or a salt thereof with a metal or basic organic nitrogen compound.

7. The method according to claim 5 wherein such compound is 3-methyl-3-(4,6-dimethoxy-1,3,5-triazin-2-yl)-1-(2-trifluormethoxy-benzene-sulphonyl)-urea or a salt thereof with a metal or basic organic nitrogen compound.

* * * * *

UNITED STATES PATENT AND TRADEMARK OFFICE
CERTIFICATE OF CORRECTION

PATENT NO. : 4,780,126

DATED : October 25, 1988

INVENTOR(S) : Hans-Joachim Diehr, et al

Page 1 of 3

It is certified that error appears in the above-identified patent and that said Letters Patent is hereby corrected as shown below:

| | |
|---|---|
| Title Page, "Abstract", line 3; Col. 98, Table 4, Heading; Col. 99, line 1; Col. 101, line 1; Col. 103, line 1, Col. 109, line 1; Col. 111, line 1; Col. 113, line 1; Col. 115, line 1; Col. 117, line 1 and Col. 119, line 1 | Delete "O" and substitute $$-\overset{\overset{O}{\|}}{C}-$$ $$-\overset{\overset{O}{\|}}{C}-$$ |
| Col. 3, line 41 | Delete "THe" and substitute --The-- |
| Col. 17, line 24 | Delete "$CH_5$" and substitute --$CH_3$-- |
| Col. 40, line 40 | Delete "-$C_2H_5$" and formula and substitute -- -$CH_3$-- and a pyrimidine ring with $CF_3$ and $OCH_3$ substituents |
| Col. 40, line 47 | Delete "-$C_2H_5$" and formula and substitute -- -$CH_3$-- and a pyrimidine ring with $CF_3$ and $CH_3$ substituents |
| Col. 74, last line | Delete "$OC_2H_3$" and substitute --$OC_2H_5$-- |

UNITED STATES PATENT AND TRADEMARK OFFICE
CERTIFICATE OF CORRECTION

PATENT NO. : 4,780,126
DATED : October 25, 1988
INVENTOR(S) : Hans-Joachim Diehr, et al It is certified that error appears in the above-identified patent and that said Letters Patent is hereby corrected as shown below:

Col. 78, line 20     Delete formula and substitute

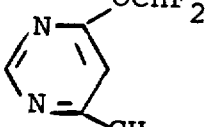

Col. 95, lines 5-6     Correct spelling of --Ischaemum--
Col. 95, line 20     Correct --orchards--
Col. 95, line 34     Delete "tht" and substitute --that--

Col. 98, Col. 99, Col. 101, Col. 103, Col. 105, Col. 107, Col. 109, Col. 111, Col. 113, Col. 115, Col. 117, and Col. 119, heading, line 2, third column of each     Delete "O" and substitute --Q--

Col. 98, line 17     Delete "2.4 b" and substitute --2.4 g--

Col. 120, line 68     Delete "1-meth-" and substitute --3-meth- --

UNITED STATES PATENT AND TRADEMARK OFFICE
CERTIFICATE OF CORRECTION

PATENT NO. : 4,780,126

DATED : October 25, 1988

INVENTOR(S) : Hans-Joachim Diehr, et al

Page 3 of 3

It is certified that error appears in the above-identified patent and that said Letters Patent is hereby corrected as shown below:

Col. 121, line 27             After "yl)-" insert -- 1- --

Signed and Sealed this

Second Day of January, 1990

*Attest:*

JEFFREY M. SAMUELS

*Attesting Officer*      *Acting Commissioner of Patents and Trademarks*